(12) United States Patent
Arai et al.

(10) Patent No.: US 10,813,556 B2
(45) Date of Patent: Oct. 27, 2020

(54) EVALUATION DEVICE, MARKET RESEARCH DEVICE, AND LEARNING EVALUATION DEVICE

(71) Applicants: DAIKIN INDUSTRIES, LTD., Osaka-shi, Osaka (JP); TOKYO INSTITUTE OF TECHNOLOGY, Meguro-ku, Tokyo (JP)

(72) Inventors: Junichiro Arai, Osaka (JP); Takashi Gotou, Osaka (JP); Makoto Iwakame, Osaka (JP); Kenichi Hino, Osaka (JP); Tomoya Hirano, Osaka (JP); Yasunori Kotani, Tokyo (JP); Yoshimi Ohgami, Tokyo (JP); Taro Tomatsu, Tokyo (JP)

(73) Assignees: Daikin Industries, Ltd., Osaka (JP); Tokyo Institute of Technology, Tokyo (JP)

( * ) Notice: Subject to any disclaimer, the term of this patent is extended or adjusted under 35 U.S.C. 154(b) by 220 days.

(21) Appl. No.: 15/767,959

(22) PCT Filed: Oct. 17, 2016

(86) PCT No.: PCT/JP2016/080755
§ 371 (c)(1),
(2) Date: Apr. 12, 2018

(87) PCT Pub. No.: WO2017/065316
PCT Pub. Date: Apr. 20, 2017

(65) Prior Publication Data
US 2018/0303350 A1  Oct. 25, 2018

(30) Foreign Application Priority Data
Oct. 15, 2015  (JP) ................................ 2015-203356

(51) Int. Cl.
  *A61B 5/01*       (2006.01)
  *G06Q 30/02*      (2012.01)
  *G06T 7/00*       (2017.01)

(52) U.S. Cl.
  CPC ............... *A61B 5/01* (2013.01); *G06Q 30/02* (2013.01); *G06Q 30/0203* (2013.01);
  (Continued)

(58) Field of Classification Search
  CPC .................... A61B 5/01; G06T 7/0012; G06T 2207/10048; G06T 2207/30088; G06Q 30/02; G06Q 30/0203
  See application file for complete search history.

(56) References Cited

U.S. PATENT DOCUMENTS 5,771,261 A * 6/1998 Anbar ...................... A61B 5/01
                                                         374/45
6,099,319 A    8/2000 Zaltman et al.
(Continued)

FOREIGN PATENT DOCUMENTS

JP    2006-305334 A    11/2006
JP    2007-68620 A      3/2007
JP    2011-65504 A      3/2011

OTHER PUBLICATIONS

International Search Report of corresponding PCT Application No. PCT/JP2016/080755 dated Nov. 8, 2016.
(Continued)

*Primary Examiner* — Paula J Stice
(74) *Attorney, Agent, or Firm* — Global IP Counselors, LLP

(57) ABSTRACT

An estimation device includes at least one of a facial skin temperature acquisition unit and a facial photographic image acquisition unit, and an evaluation unit. The facial skin temperature acquisition unit acquires, in time-series, facial
(Continued)

skin temperature data of a facial surface of a subject to which brain function activation information is provided. The facial photographic image acquisition unit obtains, in time-series, facial photographic image data obtained by imaging the facial surface of the subject to which the brain function activation information is provided. The evaluation unit evaluates a degree of interest of the subject based on at least one of the facial skin temperature data acquired by the facial skin temperature acquisition unit and the facial surface photographic image data acquired by the facial surface photographic image data acquisition unit.

11 Claims, 22 Drawing Sheets

(52) U.S. Cl.
CPC ....... *G06Q 30/0245* (2013.01); *G06T 7/0012* (2013.01); *G06T 2207/10048* (2013.01); *G06T 2207/30088* (2013.01)

(56) References Cited

U.S. PATENT DOCUMENTS

| | | |
|---|---|---|
| 2008/0065468 A1 | 3/2008 | Berg et al. |
| 2009/0080730 A1 | 3/2009 | Pavlidis |
| 2009/0157813 A1 | 6/2009 | Jung et al. |
| 2011/0020778 A1 | 1/2011 | Forbes |
| 2011/0251493 A1 | 10/2011 | Poh et al. |
| 2011/0256520 A1 | 10/2011 | Siefert |

OTHER PUBLICATIONS

Hideyuki Zenju; The Estimation of Unpleasant and Pleasant States by Nasal Thermogram; FIT (Forum on Information Technology) 2002 Ippan Koen Ronbunshu separate vol. 3; Sep. 13, 2002; pp. 459-460.

European Search Report of corresponding EP Application No. 16 85 5567.0 dated Jun. 3, 2019.

International Preliminary Report of corresponding PCT Application No. PCT/JP2016/080755 dated Apr. 26, 2018.

* cited by examiner

EVALUATION DEVICE, MARKET RESEARCH DEVICE, AND LEARNING EVALUATION DEVICE

CROSS-REFERENCE TO RELATED APPLICATIONS

This U.S. National stage application claims priority under 35 U.S.C. § 119(a) to Japanese Patent Application No. 2015-203356, filed in Japan on Oct. 15, 2015, the entire contents of which are hereby incorporated herein by reference.

TECHNICAL FIELD

The present invention relates to an evaluation device for evaluating a degree of interest of a subject, and a market research device and a learning evaluation device provided with the evaluation device.

BACKGROUND ART

In the prior art, there are devices that use electroencephalographs to estimate the brain activity of a subject and investigate the presence/absence of interest in a product or the like. An example thereof is described in Japanese Laid-open Patent Application No. 2006-305334. This device seeks to obtain honest answers about a product or the like from a subject by analyzing measurement results of the brain waves of the subject from when the subject was thinking about an answer to a question of a questionnaire.

SUMMARY

Technical Problem

By the way, preparation work is complicated when estimating the brain activity of subjects using electroencephalographs. For example, the electrodes must be pretreated before being applied to the subject.

As such, an object of the present invention is to easily estimate brain activity using an evaluation device that evaluates a degree of interest of a subject on the basis of brain activity.

Solution to the Problem

An evaluation device according to a first aspect of the present invention includes facial skin temperature acquisition means and/or facial blood circulation volume acquisition means, brain activity estimation means, and evaluation means. The facial skin temperature acquisition means acquire facial skin temperature data in time-series. The facial skin temperature data includes skin temperature data detected from the facial surface of a subject and position data of the detection site of the skin temperature data. The facial blood circulation volume acquisition means acquire facial blood circulation volume data in time-series. Photographic image data of the facial surface of the subject is captured and subjected to RGB processing in time-series. The facial blood circulation volume data is acquired on the basis of RGB data of the photographic image data obtained from the RGB processing. A plurality of components is obtained by decomposing the facial skin temperature data and/or the facial blood circulation volume data by singular value decomposition, principal component analysis, or independent component analysis. The brain activity estimation means estimate the brain activity of the subject on the basis of this plurality of components. The evaluation means evaluate a degree of interest of the subject on the basis of the brain activity of the subject estimated by the brain activity estimation means.

With the evaluation device according to the first aspect of the present invention, the brain activity of the subject is estimated on the basis of the time-series facial skin temperature data and/or facial blood circulation volume data acquired by the facial skin temperature acquisition means and/or the facial blood circulation volume acquisition means. As such, with this evaluation device, the brain activity of the subject can be estimated without using electroencephalogram electrodes or other sensors that require pretreatment before being applied. As a result, the brain activity of the subject can be easily estimated.

An evaluation device according to a second aspect of the present invention is the evaluation device of the first aspect, wherein the brain activity estimation means extract, from the plurality of components, a component having a waveform with an amplitude that has correlation with a brain activated time and a brain resting time as a determination component. Additionally, the brain activity estimation means estimate the brain activity of the subject on the basis of the determination component. With this evaluation device, a component having correlation with the brain activated time/resting time is extracted from the plurality of components as a determination component for estimating the brain activity of the subject. As such, it is possible to estimate brain activity from a component presumed to be highly related to the brain activity of the subject.

An evaluation device according to a third aspect of the present invention is the evaluation device of the first or second aspect, wherein the facial skin temperature data acquisition means and/or the facial blood circulation volume acquisition means at least acquire the facial skin temperature data and/or the facial blood circulation volume data of the forehead and/or the area around the paranasal sinuses of the subject.

The brain has a mechanism called the selective brain cooling system whereby the brain is cooled independently of body temperature. The selective brain cooling system is known to discharge heat generated by brain activity using the areas around the forehead and the paranasal sinuses. Additionally, the facial skin temperature is thought to be proportional to the facial blood circulation volume.

With the evaluation device according to the third aspect of the present invention, the brain activity of the subject is estimated on the basis of the time-series facial skin temperature data and/or facial blood circulation volume data of the forehead and/or the area around the paranasal sinuses, which is presumed to reflect brain activity. As such, with this evaluation device, the brain activity of the subject can be accurately estimated.

An evaluation device according to a fourth aspect of the present invention is the evaluation device of any one of the first to the third aspects, wherein the facial skin temperature data acquisition means and/or the facial blood circulation volume acquisition means collectively acquire the facial skin temperature data and/or the facial blood circulation volume data of a plurality of subjects. As a result, with this evaluation device, the degrees of interest of the plurality of subjects can be evaluated at once.

An evaluation device according to a fifth aspect of the present invention is the evaluation device of any one of the first to the fourth aspects, wherein the evaluation means include an analysis unit and a notification unit. The analysis unit analyzes a concentration level of the subject on the basis of the brain activity of the subject. The notification unit notifies an administrator of the evaluation means of information about the concentration level of the subject. With this evaluation device, the administrator can recognize the concentration level of the subject.

A market research device according to a sixth aspect of the present invention includes the evaluation device of any one of the first to the fifth aspects, and market research storage means. The market research storage means store results evaluated by the evaluation means for each preset research period. With this market research device, it is possible to carry out market research by analyzing the degree of interest of the subject in a product or the like. Here, the degree of interest is evaluated on the basis of the brain activity of the subject, which is estimated by the brain activity estimation means.

A learning evaluation device according to a seventh aspect of the present invention includes the evaluation device of any one of the first to the fifth aspects, and learning evaluation storage means that store results evaluated by the evaluation means for each preset learning period. With this learning evaluation device, it is possible to evaluate the degree of interest in learning matter by analyzing the degree of interest of the subject in the learning matter on the basis of the brain activity of the subject, which is estimated by the brain activity estimation means.

A market research device according to an eighth aspect of the present invention is the market research device of the sixth aspect of the present invention, further includes a display device that displays visual information about a product or the like. By installing this display device in various types of commercial facilities, the degree of interest of the subject in a predetermined product or the like can be easily evaluated.

Advantageous Effects of the Invention

With the evaluation device according to the first aspect of the present invention, the brain activity of the subject can be easily estimated.

With the evaluation device according to the second aspect of the present invention, it is possible to estimate the brain activity on the basis of a component presumed to be highly related to the brain activity of the subject.

With the evaluation device according to the third aspect of the present invention, the brain activity of the subject can be accurately estimated.

With the evaluation device according to the fourth aspect of the present invention, the degrees of interest of the plurality of subjects can be evaluated at once.

With the evaluation device according to the fifth aspect of the present invention, the administrator can recognize the concentration level of the subject.

With the evaluation device according to the sixth aspect of the present invention, market research can be carried out by analyzing the degree of interest of the subject in a product or the like.

With the learning evaluation device according to the seventh aspect of the present invention, the degree of interest of the subject in the learning matter can be evaluated.

With the market research device according to the eighth aspect of the present invention, the degree of interest of the subject in the predetermined product or the like can be easily evaluated.

DESCRIPTION OF EMBODIMENTS

Figure 1B:
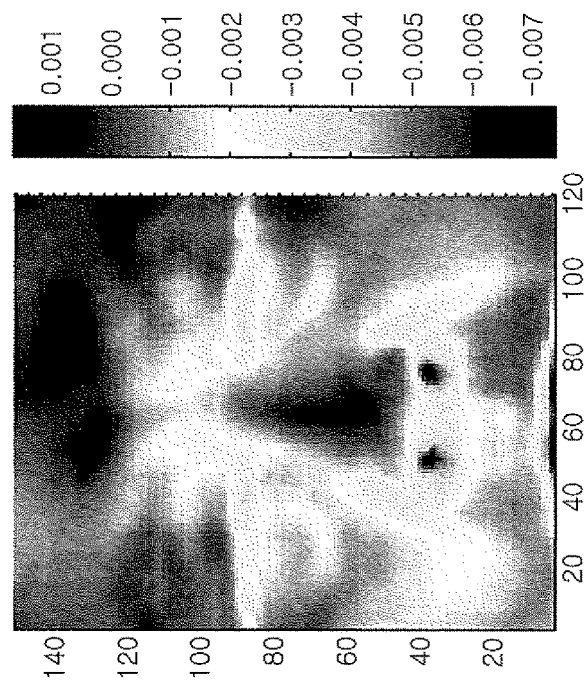
FIGS. 1A and 1B illustrate an example of photographic image data and the results of analyzing the same.

Before describing the embodiments of the present invention, the findings made by the inventors that served as an important foundation for the inventors to contrive the present invention will be described.

(1) Summary of Findings Made by the Inventors

It is known that human intellectual activity (cognitive activity and the like) and emotional activity (activity such as pleasure/displeasure) are reflected in human brain activity. Attempts to estimate human brain activity have been made in the past, but in most cases, the attempts involved using data detected by electroencephalography, magnetic resonance imaging, and/or near infrared spectroscopy.

In cases where, for example, electroencephalography is adopted as the detection method, it is necessary to attach brain wave electrodes to the subject. Additionally, resistance that occurs between the skin and the electrodes when the brain wave electrodes are attached must be reduced. Consequently, a procedure such as a process to abrade the skin or an application of a paste to the electrodes needs to be carried out. In cases where functional magnetic resonance imaging is adopted, there are restrictions on measurement conditions, such as the impossibility of measurement at any location other than an MRI room and the inability to bring metal into the measurement room. In cases where near infrared spectroscopy is adopted, a probe needs to be attached to the subject. However, wearing the probe for a long time can be painful to the subject and, in some cases, due to the contact state between the hair of the subject and the probe, the detections by the probe may not be accurate. Thus, when using conventional detection methods to measure human brain activity, a significant burden is imposed on the subject, specifically, pretreatment is needed to attach the brain wave electrodes, probes, etc., and/or the measurement conditions are limited.

Accordingly, there is a need to develop an approach whereby the burden on the subject can be reduced and also whereby human brain activity can be easily estimated.

The inventors postulated that it might be possible to estimate human brain activity on the basis of human facial skin temperature or the state of facial blood circulation, which is thought to be proportional to the facial skin temperature. Human facial skin temperature can be acquired using a measurement device such as a thermography device. The state of facial blood circulation, that is, facial blood circulation volume can be estimated from RGB data of photographic images of the facial surface, which is obtained using an imaging device. The facial skin temperature and/or photographic images of the facial surface can be acquired without using electroencephalogram electrodes, probes, or other sensors that require pretreatment before being applied.

However, it is known that human facial skin temperature changes under the influence of various factors such as outside air temperature and/or autonomic nervous activity. As such, when attempting to estimate brain activity on the basis of the facial skin temperature or on the basis of the facial blood circulation volume, which is thought to be proportional to the facial skin temperature, it is very difficult to determine whether only brain activity is reflected in the acquired data.

After much research, the present inventors discovered that it is possible to identify a component indicating a change in the facial skin temperature or a change in the facial blood circulation volume in brain activity by: detecting the facial skin temperature; decomposing, into a plurality of components, time-series facial skin temperature data including the detected temperature data and position data (coordinate data) of the detection site, or decomposing, into a plurality of components, time-series facial blood circulation volume data calculated on the basis of RGB data obtained from time-series photographic image data of the facial surface, by singular value decomposition, principal component analysis, or independent component analysis; and analyzing the plurality of the decomposed components. Thus, the present inventors conceived the present invention, in which the brain activity of the subject is estimated and analyzed, thereby enabling the evaluation of the degree of interest of the subject on the basis of the estimated brain activity.

(2) Acquisition Method of Various Facial Data and Analysis Method of Acquired Various Facial Data (2-1) Acquisition Method of Facial Skin Temperature Data and Analysis Method of Facial Skin Temperature Data Next, a description is given of an acquisition method of facial skin temperature data and analysis method of facial skin temperature data used by the present inventors to reach the findings described above.

In this test, facial skin temperature data was acquired from six subjects. Specifically, each subject was seated in a chair placed in an artificial climate room maintained at a room temperature of 25° C., and facial skin temperature data was acquired from the entire facial surface of the subject using an infrared thermography device. The infrared thermography device was capable of detecting infrared radiant energy emitted from the subject using an infrared camera, converting the detected infrared radiant energy to a facial temperature (herein, the temperature in Celsius) of the subject, and displaying and/or storing a temperature distribution thereof as facial skin temperature data (e.g. image data representing the temperature distribution). In this test, an R300 (manufactured by NEC Avio Infrared Technologies Co., Ltd.) was used as the infrared thermography device. The infrared camera was set in front of the subject at a position 1.5 m away from the subject. The facial skin temperature data was acquired for 30 minutes.

Additionally, in this test, brain function activation tasks were given to the subjects while the facial skin temperature data was being acquired. Thus, facial skin temperature data during brain resting time and facial skin temperature data during brain activated time were acquired. The brain function activation tasks were presented to the subjects as images on a display device or the like. Examples thereof included calculation, recognition of numbers, shapes, and colors, memorization of symbols, letters, and language, and other psychological tasks. In this test, mental multiplication was used as the brain function activation task. The subjects were instructed to multiply numbers displayed in longhand on the display device, and input answers using a keyboard. In this test, the brain function activation tasks were continuously given to the subjects for ten minutes after five minutes had elapsed since the start of acquiring the facial skin temperature data.

To analyze the facial skin temperature data, the acquired facial skin temperature data was subjected to singular value decomposition. Here, Singular Value Decomposition (SVD) of MATLAB (registered trademark) was used as the analysis tool. In the singular value decomposition, the target was set as all of the time-series facial skin temperature data acquired (30-minutes of data), the factor was set as time data of every 30 seconds (60 time points for 30 minutes), and the measure was set as the facial skin temperature data (240×320 pixels) during each period (the 30 seconds). The facial skin temperature data X was decomposed into a plurality of components by singular value decomposition. Then, for each component, a time distribution V, a space distribution U, and a singular value S representing the magnitude of the component were calculated. The relationships between these values is expressed in the following equation. Note that V' is a matrix obtained by interchanging the columns and rows of V.

$$X=(U*S)*V'$$ Equation 1

Then, the time distribution V and the space distribution U of each component resulting from the singular value decomposition were plotted on graphs to create a component waveform diagram and a temperature distribution diagram for each component.

Furthermore, the component waveform diagram and the temperature distribution diagram for each component were analyzed to identify a component indicating a change in skin temperature that reflects brain activity.

The component waveform diagram for each component was analyzed to determine the presence/absence of correlation between the amplitude of the component waveform and each of the brain resting time and the brain activated time. Specifically, evaluations were conducted as to whether or not correlation existed between the amplitude shown in the component waveform diagram for each component and the brain resting time period/brain activated time period. In this test, during the period of acquiring the facial skin temperature data, the brain resting time was defined as a period of five minutes from the start of data acquisition and a period of 15 minutes from a point in time 15 minutes had elapsed since the start point of data acquisition to the end of data acquisition. These were periods in which the brain function activation task was not given to the subjects. Additionally, the brain activated time was defined as a period of 10-minutes from a point in time occurring after five minutes had elapsed since the start of data acquisition, up to a point in time after 10 minutes had elapsed. This was a period in which the brain function activation task was being given to the subjects. Then, evaluations were conducted to determine the presence/absence of correlation between the amplitude shown in the component waveform diagram for each component and each of the brain resting time and the brain activated time. Note that statistical correlation analysis was performed to determine the presence/absence of correlation. When the significance level (a) was 0.05 or lower, it was determined that correlation existed.

The temperature distribution diagram for each component was analyzed to determine the presence/absence of temperature changes at a predetermined site on the facial surface. The brain has a mechanism called the selective brain cooling system whereby the brain is cooled independently of body temperature. The selective brain cooling system is known to discharge heat generated by brain activity using the forehead and the area around the paranasal sinuses (including the area between the eyebrows and the area around the nose). As such, in this test, the temperature distribution diagram for each component was evaluated to determine the presence/absence of temperature changes at the forehead and the area around the paranasal sinuses. Note that, in the temperature distribution diagrams, the presence/absence of temperature changes at the forehead and the area around the paranasal sinuses was evaluated on the basis of visual inspection, or on the basis of whether or not the temperatures of the forehead and the area around the paranasal sinuses differed one standard deviation (SD) or more from the average temperature of all measurement data of the temperatures of the forehead and the area around the paranasal sinuses.

Additionally, polarity (positive or negative) of the facial skin temperature data X is determined by the relationships between the values of the space distribution U, the singular value S, and the time distribution V. As such, in some cases, polarity may appear inverted in the temperature distribution diagram and the component waveform diagram for each component. Therefore, polarity was not considered when evaluating the component waveform diagrams and the temperature distribution diagrams.

As described above, in this case, the infrared thermography device converts the infrared radiant energy detected from the subject into temperatures, and uses the temperature distribution thereof as the facial skin temperature data. However, when acquiring the facial skin temperature of a human subject using the infrared thermography device, various temperature changes unrelated to brain activity (i.e. noise), such as facial movements and/or autonomic nervous activity, are also acquired as the facial skin temperature data (see FIG. 1A). Therefore, in order to detect such temperature changes that are unrelated to brain activity, relative facial skin temperature data was created for which an average of all of the temperature data included in the facial skin temperature data of every 30 seconds is set to "0", the created facial skin temperature data was also subjected to singular value decomposition in which the SVD of MATLAB (registered trademark) is used as the analysis tool, a component waveform diagram and a temperature distribution diagram for each component were created in accordance with the singular value S, and the diagrams were analyzed to identify a component indicating a change in skin temperature that reflects brain activity.

For the sake of convenience, in the following description, the facial skin temperature data, acquired by the infrared thermography device, is referred to as "facial skin temperature data based on temperature conversion data"; and the relative facial skin temperature data, for which the average of all of the temperature data included in the facial skin temperature data based on temperature conversion data obtained every predetermined time period (every 30 seconds in this test) is set to "0", is referred to as "facial skin temperature data based on relative temperature conversion data."

Additionally, for one of the six subjects, in addition to detecting the facial skin temperature using the infrared thermography device, electrodes were connected to the scalp of the subject and electroencephalograms were taken. An evaluation was conducted for correlation between the amplitude of the component waveform diagram and the amplitude of the β wave, which is known as a waveform that appears when awake or when the consciousness is nervous (brain wave in the 14 to 30 Hz frequency range). Note that, when taking the electroencephalogram, the electrodes were arranged at six sites (F3, F4, C3, C4, Cz, and Pz) specified by the International 10-20 System.

It can be expected that the head of the subject may move vertically while the brain function activation task is given to the subject. If such movement occurs, the position of the face of the subject with respect to the infrared camera will change. Therefore, a control test was conducted on one subject in order to verify whether such changes in the position of the face influence the changes in skin temperature. In the control test to verify the influence of movement of the subject when acquiring the facial skin temperature data, the same infrared thermography device used in the test described above was used to acquire the facial skin temperature data of the subject. However, in this case, the subject was instructed also to operate the keyboard at random timings during the period in which the brain function activation task was not given (that is, during brain resting time). The facial skin temperature data based on temperature conversion data and the facial skin temperature data based on relative temperature conversion data acquired by the control test were also subjected to singular value decomposition in which the SVD of MATLAB (registered trademark) was used as the analysis tool, a component waveform diagram and a temperature distribution diagram for each component were created in accordance with the singular value S, and the diagrams were analyzed to identify a component indicating a change in skin temperature that reflects brain activity.

Figure 1A:
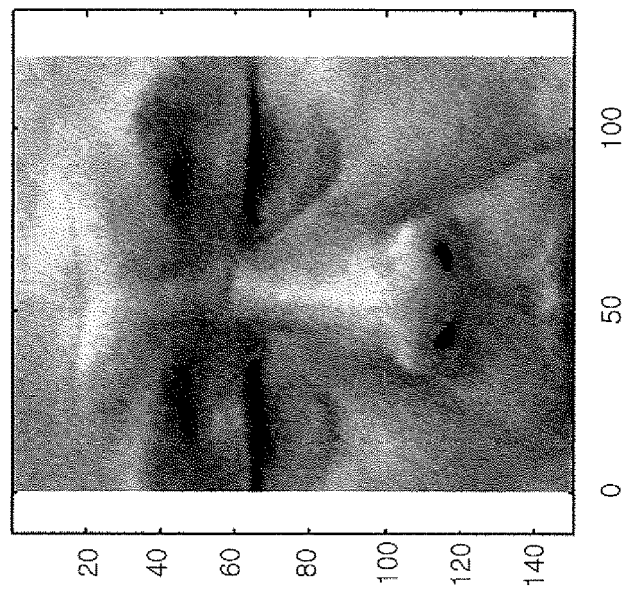

(2-2) Acquisition Method of Photographic Image Data of Facial Surface and Analysis Method of Photographic Image Data of Facial Surface FIG. 1A illustrates an example of photographic image data, captured using the imaging device, of the area around the paranasal sinuses of the facial surface of a subject. FIG. 1B illustrates an example of a blood circulation volume distribution diagram (image map).

Next, a description is given of an acquisition method of photographic image data of the facial surface and an analysis method of photographic image data of the facial surface used by the present inventors to reach the findings described above.

In this test, photographic image data of the facial surface was acquired from six subjects. Specifically, each subject was seated in a chair placed in an artificial climate room maintained at a room temperature of 25° C., and photographic image data of the area around the paranasal sinuses of the entire facial surface of the subject was acquired in time-series using an imaging device capable of acquiring images in time-series.

Additionally, based on the selective brain cooling system described above, it is postulated that changes in the facial blood circulation volume, thought to be proportional to the facial skin temperature resulting from brain activity, will appear at the forehead and/or the area around the paranasal sinuses. As such, the present inventors postulated that, if the changes in the facial blood circulation volume at least at the forehead and/or the area around the paranasal sinuses could be captured, it would be possible to accurately estimate brain activity. Therefore, in this test, photographic image data of the area around the paranasal sinuses of the facial surfaces of the subjects were acquired in time-series.

Additionally, in this test, an imaging device on the liquid crystal screen side of an iPad Air (registered trademark, manufactured by Apple) was used as the imaging device, and color video data was acquired as the time-series photographic image data. This imaging device was set in front of the subject at a position 1.0 m away from the subject. Then, using the imaging device, photographic image data was continuously captured for 30 minutes at an imaging period of 30 frames/second along the time axis. Thus, video data of the facial surface was acquired.

Furthermore, in this test, the brain function activation task was given to the subjects while the video data of the facial surface was being acquired. Thus, video data of the facial surface during brain resting time and video data of the facial surface during brain activated time were acquired. In this test, as in the test described above, "mental multiplication" was used as the brain function activation task. The subjects were instructed to multiply numbers displayed in longhand on the display device, and input answers using a keyboard. However, in this test, the brain function activation tasks were continuously given to the subjects for ten minutes after five minutes had elapsed since the start of acquiring the video data of the facial surface.

To analyze the video data of the facial surface, blood circulation volume data was calculated on the basis of RGB data obtained from the captured video data of the facial surface, and the calculated time-series blood circulation volume data was subjected to singular value decomposition, in which SVD of MATLAB (registered trademark) was used as the analysis tool. Here, in accordance with the CIE-L*a*b* color system, an erythema index a* that correlates with skin redness and hemoglobin amount was calculated from the RGB data of the image, and this erythema index a* was used as the blood circulation volume data. In the singular value decomposition, the target was set as the blood circulation volume data (the erythema index in this case) based on the RGB data acquired from all of the acquired video data (30 minutes of data) in time-series, the factor was set as time data of every 30 seconds (60 time points for 30 minutes), and the measure was set as the erythema index calculated from the RGB data for each period (every 30 seconds) (the erythema index obtained by extracting frame data of one second every 30 seconds, and calculating on the basis of the average value of the RGB values obtained from the frame data; 240×320 pixels). The time-series blood circulation volume data based on the RGB data obtained from the video data of the facial surface was decomposed into a plurality of components by singular value decomposition. Then, for each component, a time distribution V, a space distribution U, and a singular value S representing the magnitude of the component was calculated. The relationships between these values are the same as those expressed in Equation 1 above.

Then, the time distribution V and the space distribution U of each component resulting from the singular value decomposition were plotted on graphs to create a component waveform diagram and a blood circulation volume distribution diagram for each component.

Furthermore, the component waveform diagram and blood circulation volume distribution diagram for each component were analyzed to identify a component indicating a change in the facial blood circulation volume, that is, an RGB change in the facial surface, that reflects brain activity.

The component waveform diagram for each component was analyzed to determine the presence/absence of correlation between the amplitude of the component waveform and the each of brain resting time and the brain activated time. Specifically, evaluations were conducted as to whether or not correlation existed between the amplitude shown in the component waveform diagram for each component and the brain resting time period/brain activated time period. In this test, during the period of acquiring the photographic image data of the facial surface, the brain resting time was defined as a period of five minutes from the start of data acquisition and a period of 15 minutes from a point in time after 15 minutes had elapsed since the start point of data acquisition to the end of data acquisition. These were periods in which the brain function activation task was not given to the subjects. Additionally, the brain activated time was defined as a period of 10-minutes from a point in time occurring after five minutes had elapsed since the start of data acquisition, up to a point in time after 10 minutes had elapsed. This was a period in which the brain function activation task was being given to the subjects. Then, evaluations were conducted to determine the presence/absence of correlation between the amplitude shown in the component waveform for each component and each of the brain resting time and the brain activated time. Note that statistical correlation analysis was performed to determine the presence/absence of correlation. When the significance level (a) was 0.01 or lower, it was determined that correlation existed.

The blood circulation volume distribution diagram for each component was analyzed to determine the presence/absence of blood circulation volume changes at a predetermined site on the facial surface. The blood circulation volume distribution diagrams were created by arranging the space distributions U, calculated by pixel, at the respective positions of the pixels. The blood circulation volume distribution diagram for each component thus created was evaluated to determine the presence/absence of changes in blood circulation volume at the forehead and the area around the paranasal sinuses. Note that, in the blood circulation volume distribution diagrams, the presence/absence of a change in blood circulation volume at the forehead and the area around the paranasal sinuses was evaluated on the basis of the presence/absence of the change in the blood circulation volume that was observed through visual inspection, or on the basis of the value of the blood circulation volume at the forehead and the area around the paranasal sinuses as shown FIG. 1B was not "0.000".

Additionally, polarity (positive or negative) of the blood circulation volume data X was determined by the relationships between the values of the space distribution U, the singular value S, and the time distribution V. As such, in some cases, polarity may appear inverted in the blood circulation volume distribution diagram and the component waveform diagram for each component. Therefore, polarity was not considered when evaluating the component waveform diagrams and the blood circulation volume distribution diagrams.

Furthermore, in order to validate the correlation between the facial skin temperature and the facial blood circulation volume, while the photographic image data of the facial surfaces of the six subjects was being acquired in time-series, the facial skin temperature data was acquired in time-series using the infrared thermography device, the acquired facial skin temperature data was subjected to singular value decomposition using the SVD of MATLAB (registered trademark) as the analysis tool, a component waveform diagram for each component was created in accordance with the singular value S, and the diagrams were analyzed to determine the presence/absence of correlation between the amplitude of the component waveform and each of the brain resting time and the brain activated time. In this test, the same device described above was used as the infrared thermography device. The infrared camera was set in front of the subject at a position 1.5 m away from the subject.

When acquiring the photographic image data of the facial surface using the imaging device, in some cases sunlight or the like strikes the facial surface while imaging, reflects off the facial surface, and this reflected light enters the lens of the imaging device. In such cases, this reflected light may be recorded in the captured photographic image data of the facial surface. Here, in the RBG data obtained from the photographic image data, changes in brightness based on the facial blood circulation volume are smaller than changes in brightness based on reflected light. Consequently, if blood circulation volume calculated on the basis of RGB data obtained from photographic image data with the reflected light recorded therein is analyzed, it is considered that the RGB changes in the facial surface unrelated to brain activity (i.e. noise) could be mixed into the data. Therefore, in order to prevent the mixing of such RGB changes in the facial surface that were unrelated to brain activity, relative blood circulation volume data was created from relative RGB data obtained by setting an average of all of the RGB data taken every 30 seconds at "0". Then, the thus-created blood circulation volume data was also subjected to singular value decomposition using the SVD of MATLAB (registered trademark) as the analysis tool, and the component waveform diagram and the blood circulation volume distribution diagram for each component were created in accordance with the singular value S. Then, the diagrams are analyzed to identify a component indicating the RGB change of the facial surface that reflects brain activity.

For the sake of convenience, in the following description, the relative blood circulation volume data based on relative RGB data, for which the average of all of the RGB data obtained every predetermined time period (every 30 seconds in this test) is set to "0", is referred to as "relative conversion blood circulation volume data"; whereas the blood circulation volume data based on the RGB data before converting to the relative RGB data is referred to simply as "blood circulation volume data."

Additionally, while acquiring the time-series photographic image data of the facial surfaces of the six subjects using the imaging device, electrodes were connected to the scalps of the subjects and electroencephalogram were taken. Evaluations were conducted for correlation between the amplitude of the component waveform diagrams and the amplitude of the β wave, which are known as a waveform that appears when awake or when brain cells are active (brain waves in the 13 to 30 Hz frequency range). Note that, when taking the electroencephalograms, the electrodes were arranged at 19 sites (Fp1, Fp2, F3, F4, C3, C4, P3, P4, O1, O2, F7, F8, T3, T4, T5, T6, Fz, Cz, and Pz) on the scalp specified by the International 10-20 System.

Furthermore, it can be expected that the heads of the subjects may move vertically while the brain function activation task is given to the subjects. If such movement occurs, the positions of the faces of the subjects with respect to the imaging device will change. A control test was conducted on one subject in order to verify whether such changes in the position of the face influence the RGB changes in the facial surface. In the control test, as in the test described above, the imaging device was used to acquire the time-series photographic image data of the facial surface of the subject. However, in this case, the subject was instructed to operate the keyboard at random timings during the period in which the brain function activation task was not given (that is, during brain resting time). Furthermore, the time-series blood circulation volume data, based on the RGB data obtained from the time-series photographic image data of the facial surface captured in the control test, was subjected to singular value decomposition using the SVD of MATLAB (registered trademark) as the analysis tool, a component waveform diagram for each component was created in accordance with the singular value S. Then, the diagrams were analyzed to determine the presence/absence of correlation between the amplitude of the component waveform and each of the brain resting time and the brain activated time. Additionally, an analysis was conducted to determine the presence/absence of correlation between the amplitude of each component waveform and actual facial movement. The actual facial movement was evaluated by acquiring, from the photographic image data, a two-dimensional coordinate of a point corresponding to an actual point at the face, and calculating a movement distance of the face every 30 seconds when imaging. In these calculations, the photographic image data at the start of the control test was used as a reference. Furthermore, an analysis was also conducted to determine the presence/absence of correlation between the amplitude of each component waveform and the number of inputs on the keyboard during imaging. The number of inputs on the keyboard during imaging was evaluated by calculating a simple moving average every 30 seconds in the time-series photographic image data.

(3) Analysis Results (3-1) Facial Skin Temperature Data Analysis Results

Figure 2A:
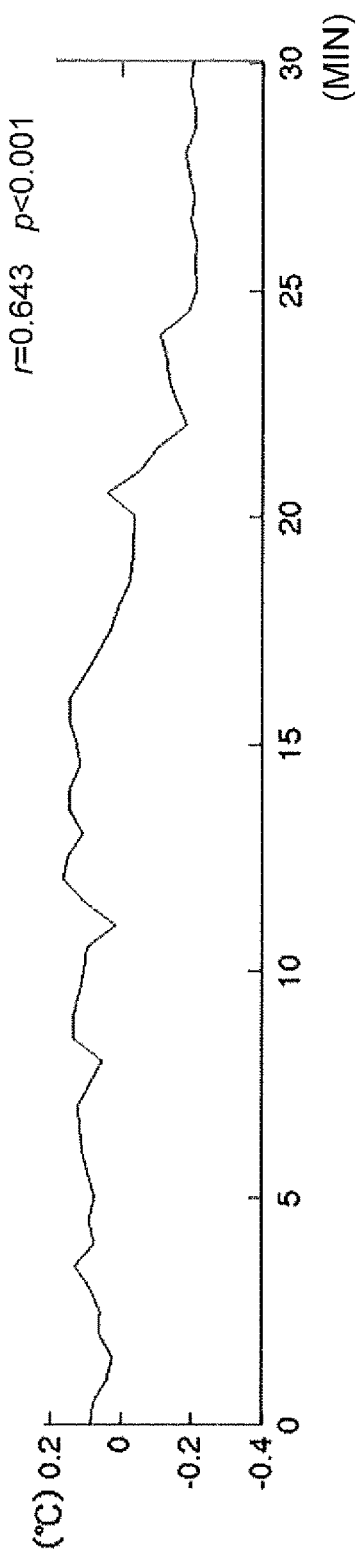
FIGS. 2A and 2B illustrate a portion of the results of analyzing facial skin temperature data.
Figure 2B:
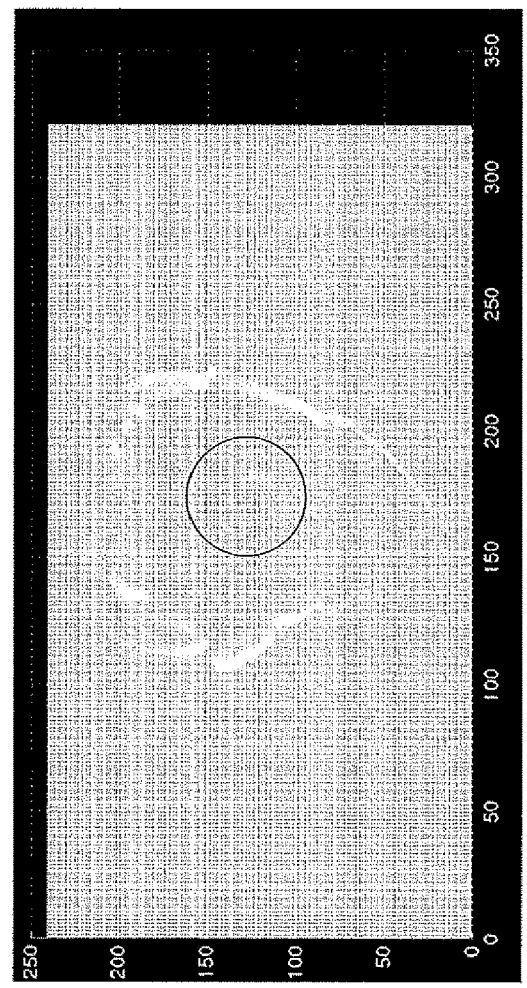
Figure 3A:
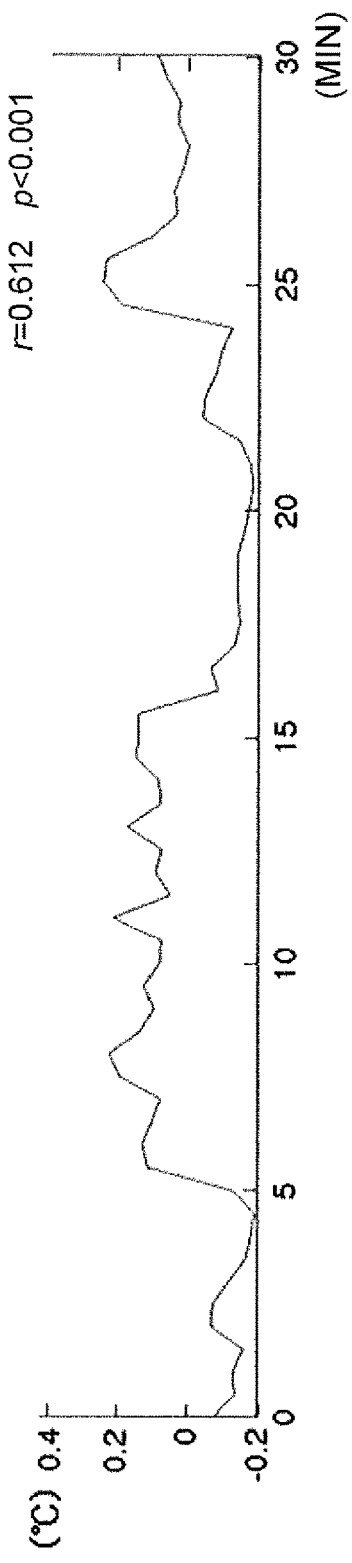
FIGS. 3A and 3B illustrate a portion of the results of analyzing the facial skin temperature data.
Figure 3B:
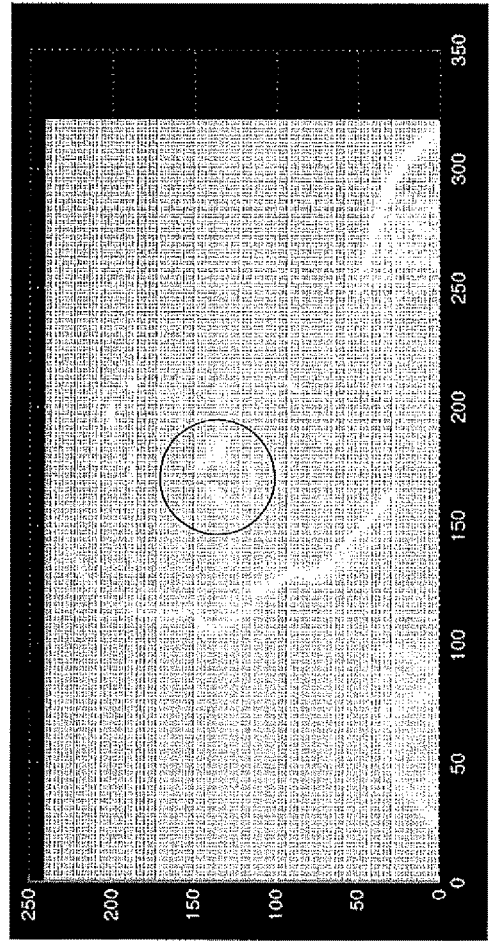
Figure 4:
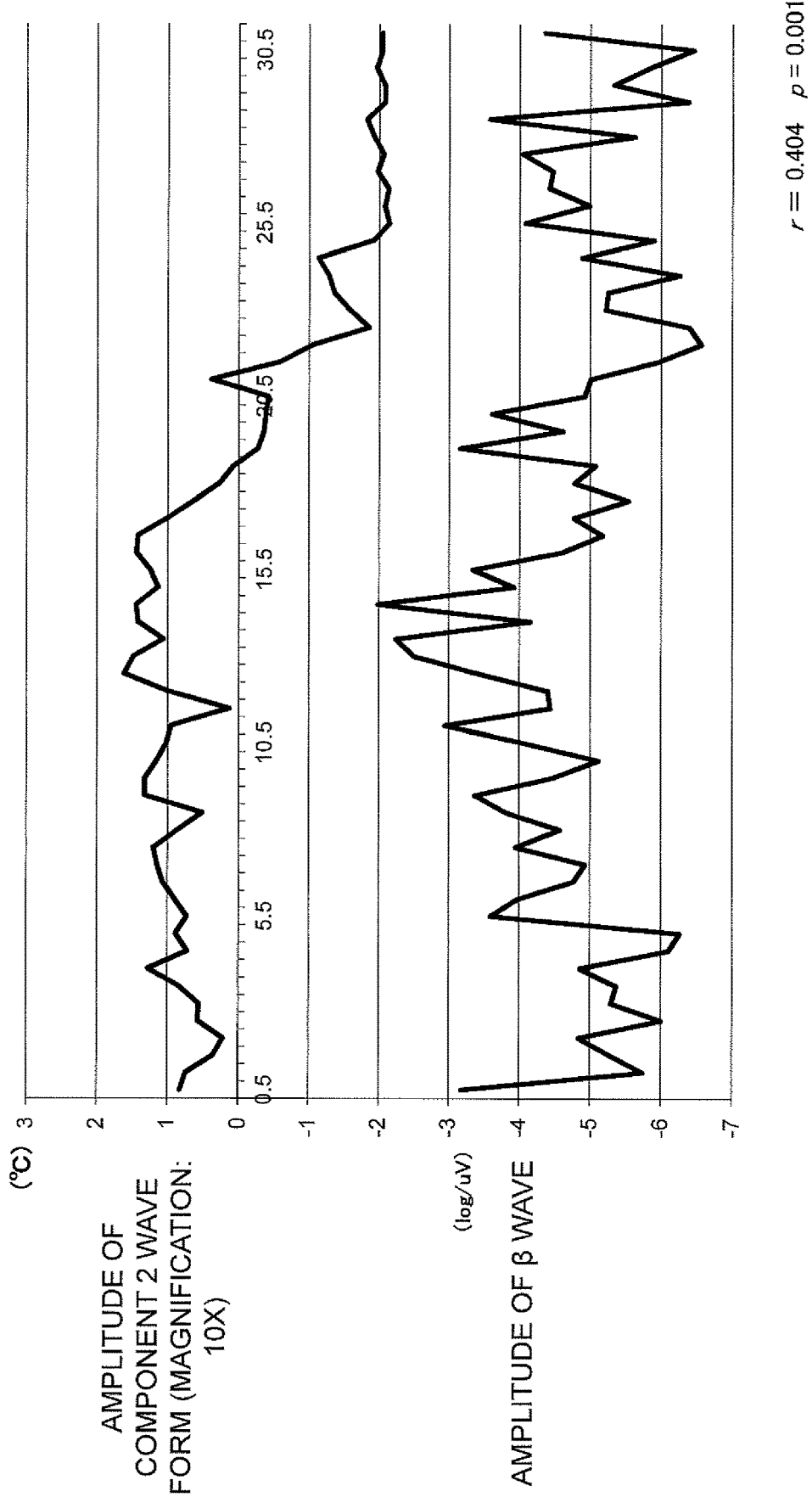
FIG. 4 is a chart illustrating the amplitude of a component waveform of a component 2, and the amplitude of the β wave of the measured brain waves.
Figure 5:
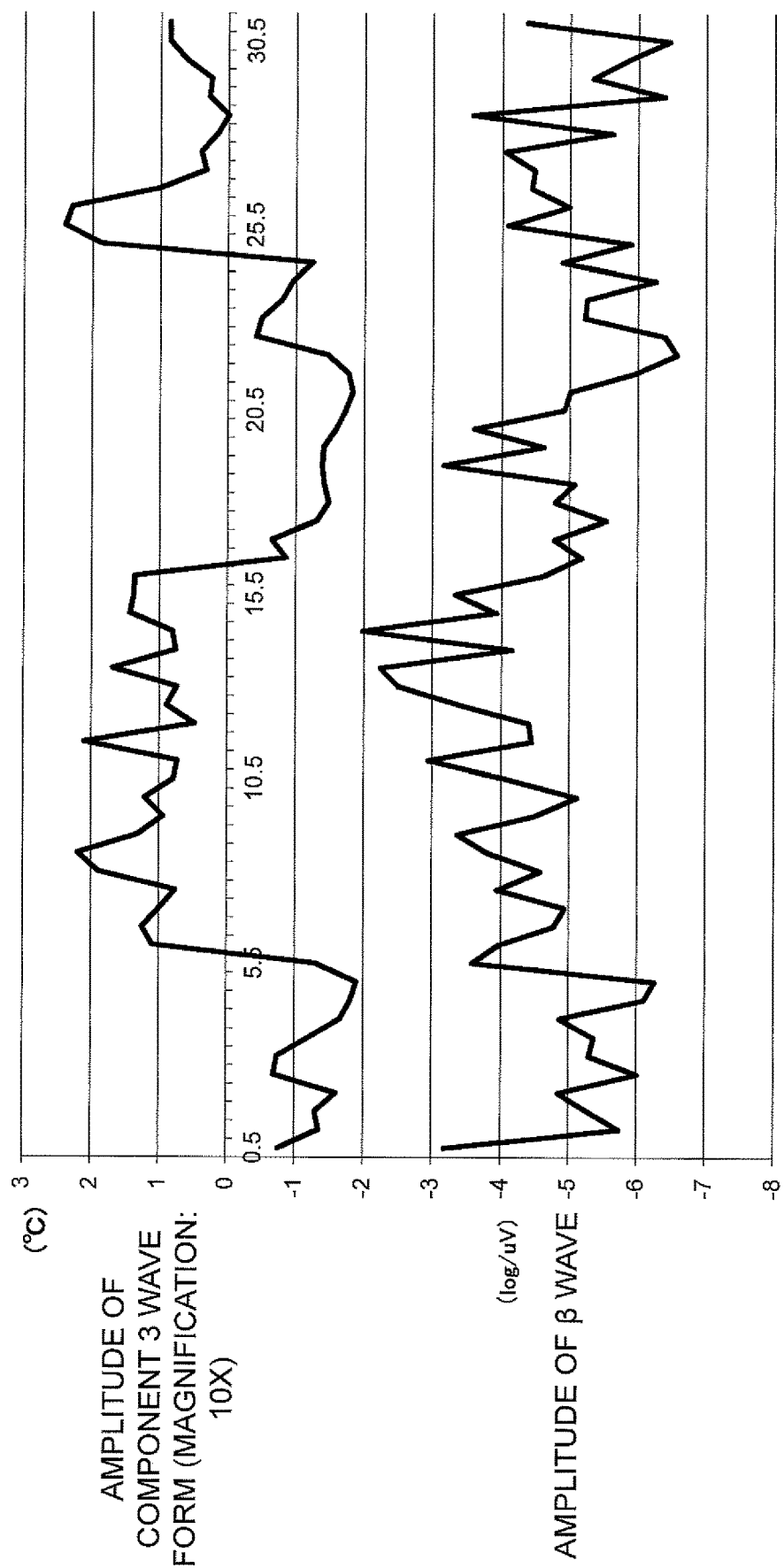
FIG. 5 is a chart illustrating the amplitude of a component waveform of a component 3, and the amplitude of the β wave of the measured brain waves.
Figure 6A:
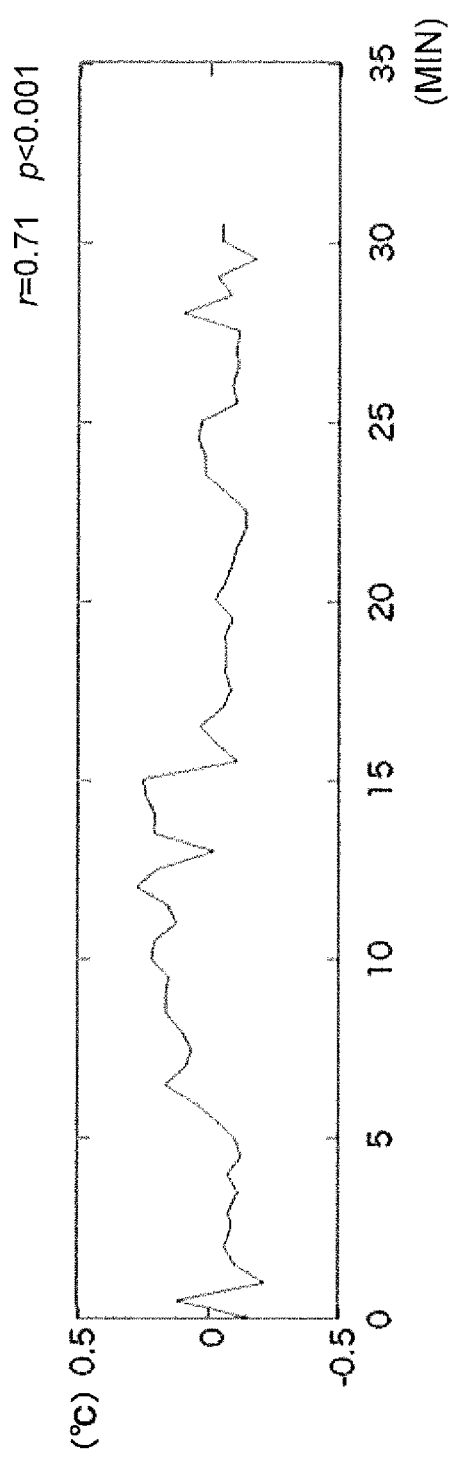
FIGS. 6A and 6B are a chart illustrating a portion of the results of analyzing the facial skin temperature data obtained in a control test.
Figure 6B:
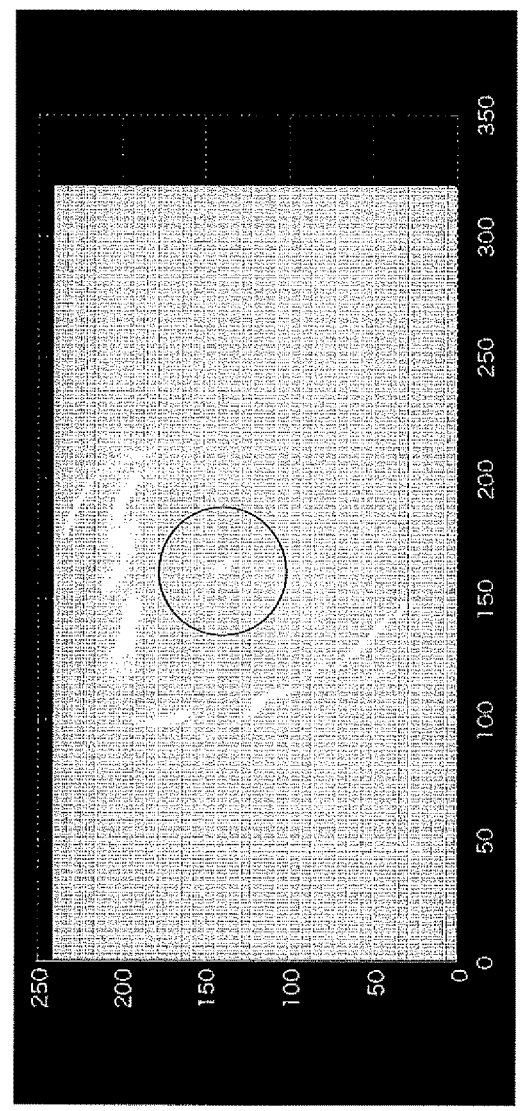

FIG. 2 illustrates a portion of the results of analyzing the facial skin temperature data based on the temperature conversion data. FIG. 2A illustrates the component waveform diagram of a component 2 of a subject 1. FIG. 2B illustrates the temperature distribution diagram of the component 2 of the subject 1. FIG. 3A illustrates the component waveform diagram of a component 3 of the subject 1. FIG. 3B illustrates the temperature distribution diagram of the component 3 of the subject 1. FIGS. 4 and 5 illustrate relationships between the amplitudes of the component waveforms and brain waves. FIG. 4 illustrates the amplitude of the component waveform of the component 2 of the subject 1, and the amplitude of the β wave of the measured brain waves. FIG. 5 illustrates the amplitude of the component waveform of the component 3 of the subject 1, and the amplitude of the β wave of the measured brain waves. FIGS. 6A and 6B illustrate a portion of the results of analyzing the facial skin temperature data obtained in the control test. FIG. 6A illustrates the component waveform diagram of the component 3. FIG. 6B illustrates the temperature distribution diagram of the component 3.

Table 1 shows the results of analyzing the facial skin temperature data for each subject.

From the results obtained by analyzing the facial skin temperature data described above, significant correlation was found between human brain activity and the component 2 and/or the component 3 of the plurality of components obtained by decomposing the time-series facial skin temperature data by singular value decomposition.

between the amplitude of the β wave of the brain waves and the amplitudes of the component 2 and the component 3.

Furthermore, in the control test, even in states where the subject moved while the facial skin temperature data was being acquired, there was significant correlation between the component 3 and human brain activity (see FIG. 6). From these results, it was found that movement by the subject when acquiring the facial skin temperature data does not influence the component 3 of the plurality of components.

Based on these results, the present inventors made the following findings.

The time-series facial skin temperature data acquired from the subjects were decomposed into the plurality of components by singular value decomposition. As a result of analyzing each of the decomposed components, it was found that the component 3 of the plurality of components is a component that is related to brain activity. Specifically, it was found that it is possible to identify a component indicating a change in skin temperature that reflects brain activity from the plurality of components by decomposing the time-series facial skin temperature data into the plurality of components by singular value decomposition, extracting components having correlation with the activation/resting of the brain from the decomposed plurality of components, and analyzing the extracted components using the selective brain cooling system. Thus, the present inventors found that it is possible to estimate brain activity on the basis of human facial skin temperature.

(3-2) Results of Analyzing Photographic Image Data of Facial Surface

Figure 7:
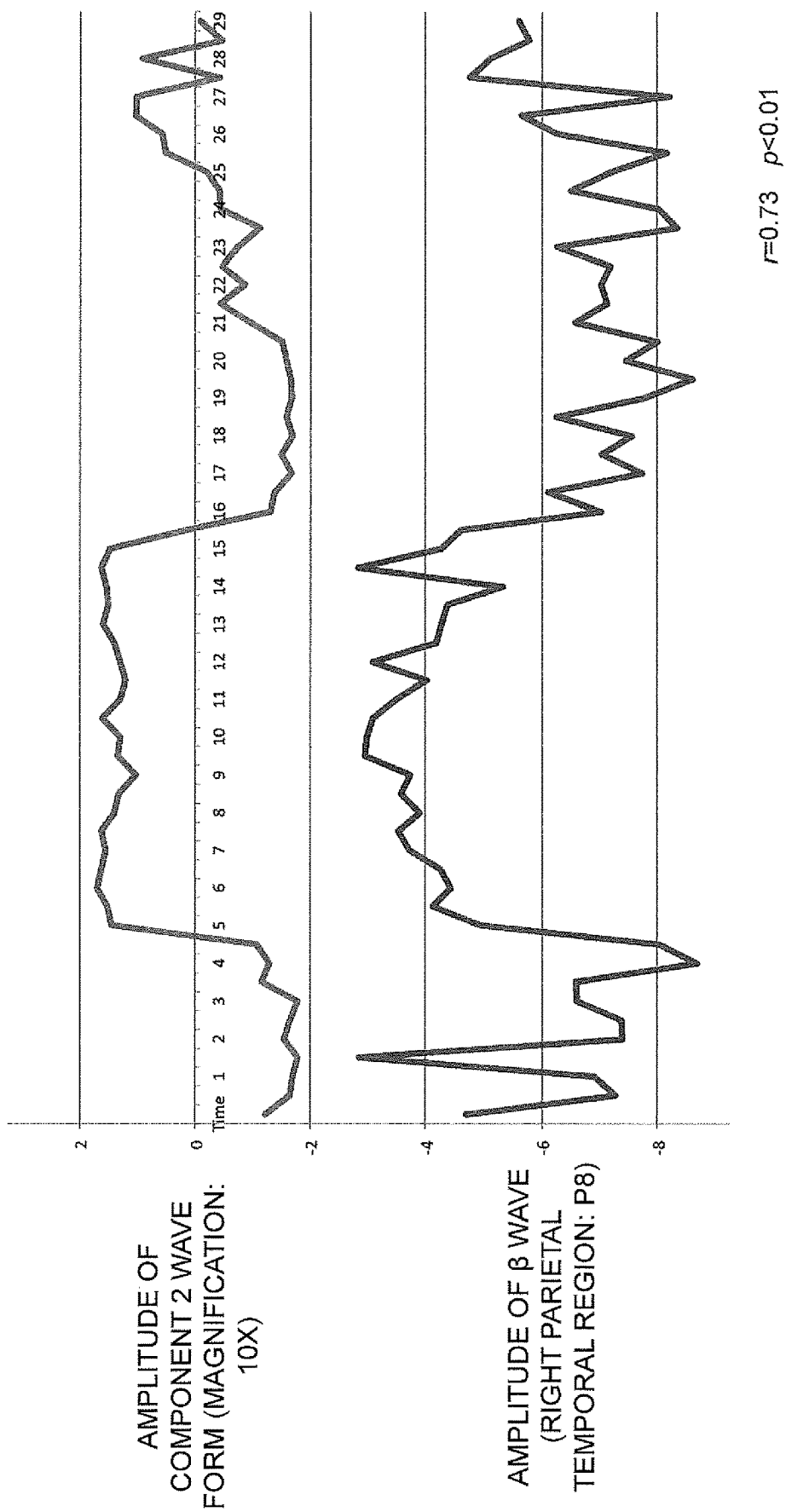
FIG. 7 is a chart illustrating a component waveform based on photographic image data of the facial surface, and the amplitude of the β wave of the measured brain waves.
Figure 8:
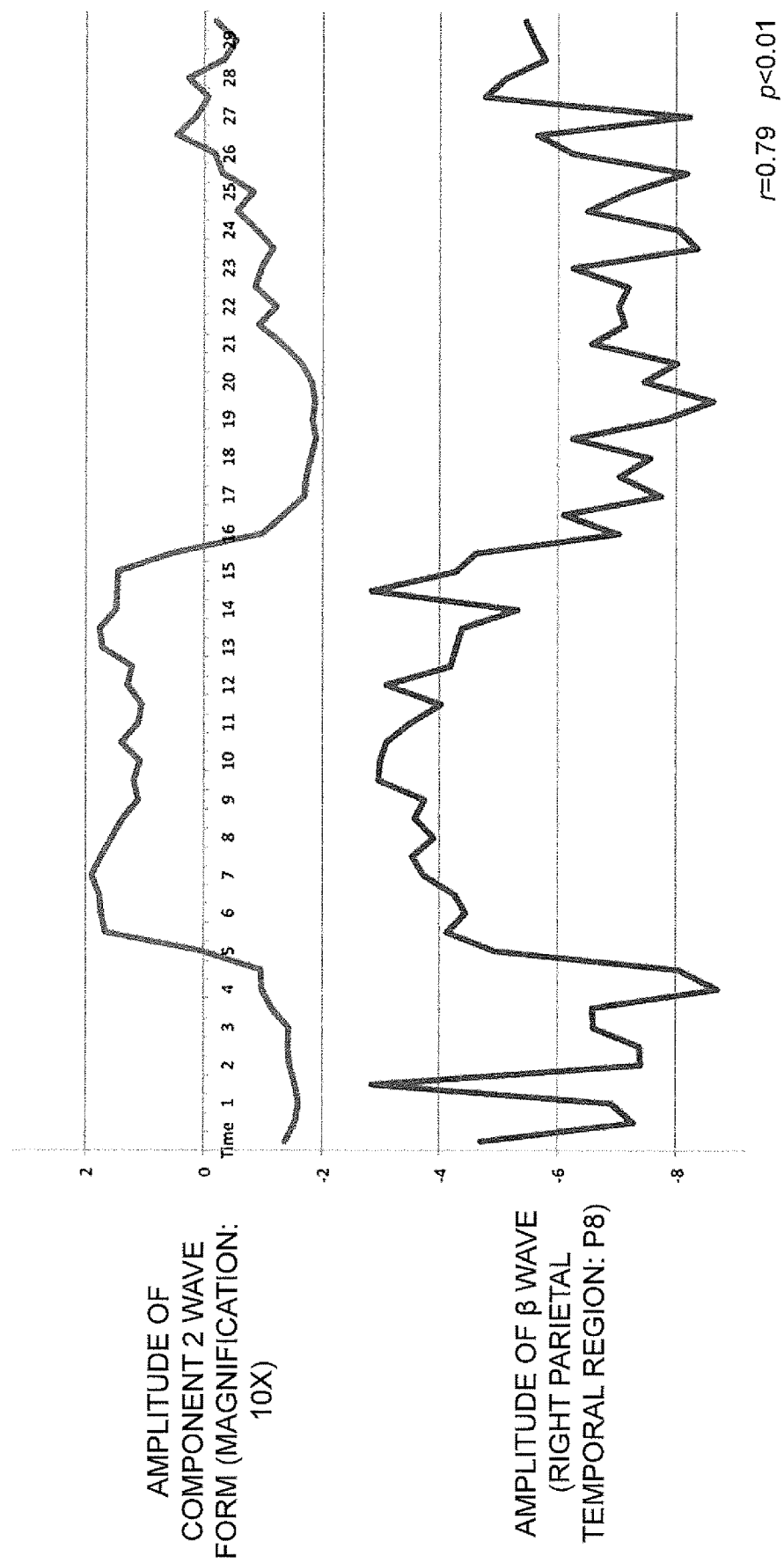
FIG. 8 is a chart illustrating a component waveform based on facial skin temperature data and the amplitude of the β wave of the measured brain waves.
Figure 9:
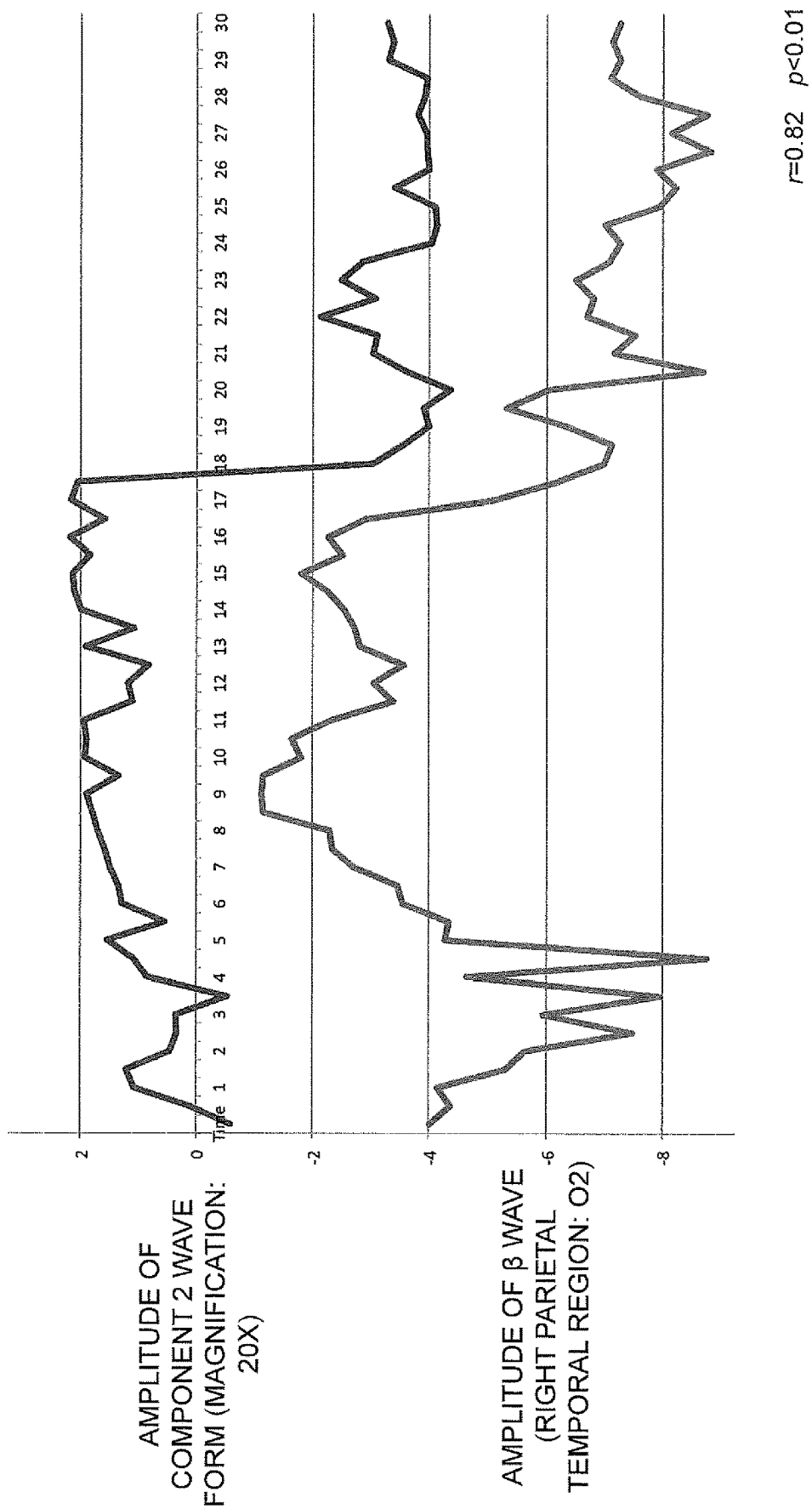
FIG. 9 is a chart illustrating a component waveform based on photographic image data of the facial surface, and the amplitude of the β wave of the measured brain waves.

FIGS. 7 to 18 illustrate portions of the results of comparing-analyzing component waveform diagrams based on the photographic image data of the facial surface (blood circulation volume data) or facial skin temperature data, and the waveform diagrams of the β wave of the measured brain waves. FIG. 7 illustrates the amplitude of the component waveform of the component 2 based on the photographic image data of the subject 1, and the amplitude of the β wave of the measured brain waves of the subject 1. FIG. 8 illustrates the amplitude of the component waveform of the component 2 based on the facial skin temperature data of the subject 1, and the amplitude of the β wave of the measured brain waves of the subject 1. FIG. 9 illustrates the amplitude of the component waveform of the component 2 based on

TABLE 1

| Subject | Correlation in Data Based on Absolute Temperature Conversion Data | | Correlation in Data Based on Relative Temperature Conversion Data | |
|---|---|---|---|---|
| | Component waveform | Temperature distribution | Component waveform | Temperature distribution |
| Subject 1 | Component 2, Component 3 | Component 2, Component 3 | Component 2, Component 3 | Component 2, Component 3 |
| Subject 2 | Component 3 | Component 3 | Component 3 | Component 3 |
| Subject 3 | Component 1, Component 2, Component 3 | Component 2, Component 3 | Component 2, Component 3 | Component 2, Component 3 |
| Subject 4 | Component 2, Component 3 | Component 2, Component 3 | Component 2, Component 3 | Component 2, Component 3 |
| Subject 5 | Component 2, Component 3 | Component 2, Component 3 | Component 2, Component 3 | Component 2, Component 3 |
| Subject 6 | Component 2, Component 5 | Component 2, Component 5 | Component 2, Component 5 | Component 2, Component 5 |

Figure 10:
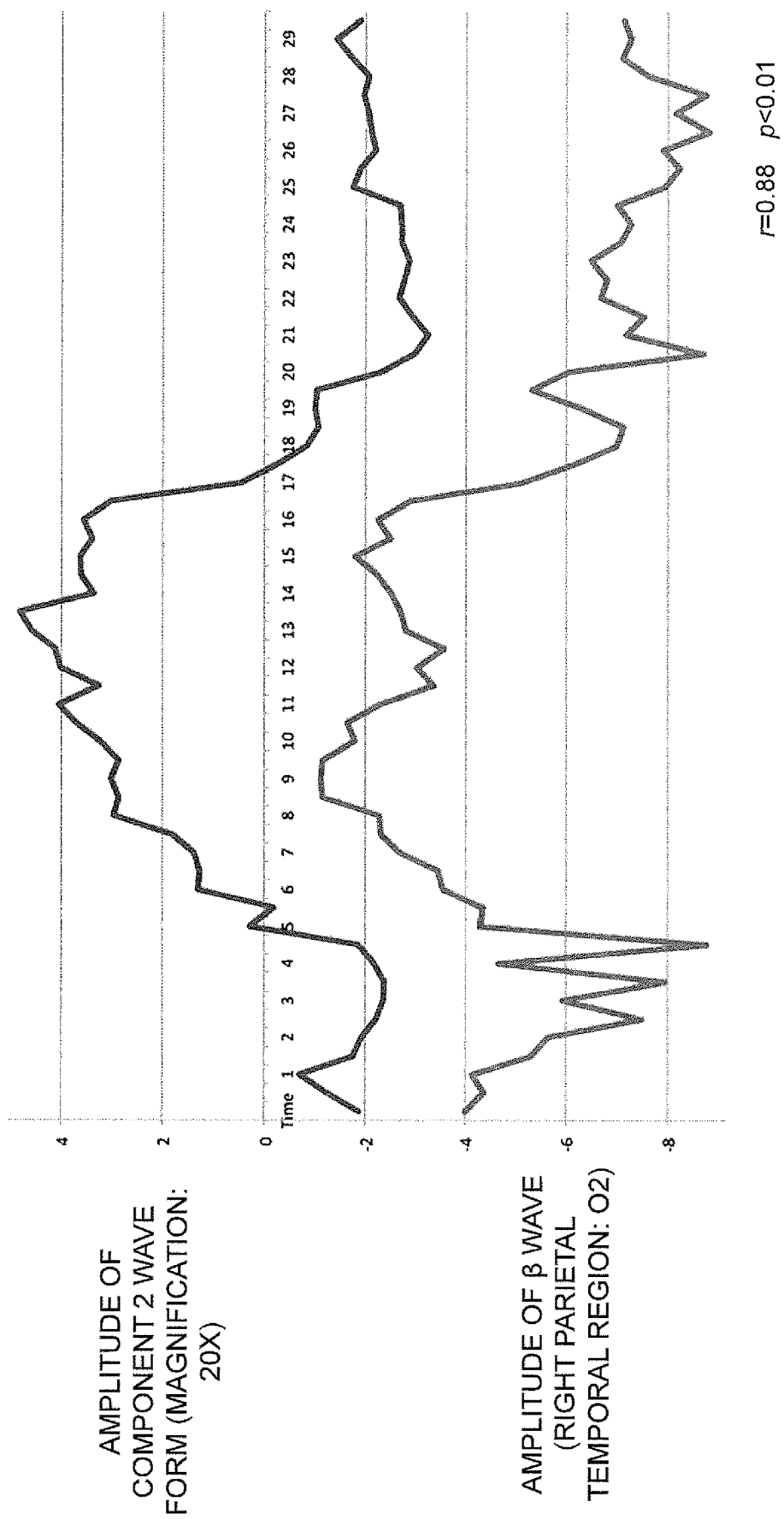
FIG. 10 is a chart illustrating a component waveform based on facial skin temperature data, and the amplitude of the β wave of the measured brain waves.
Figure 11:
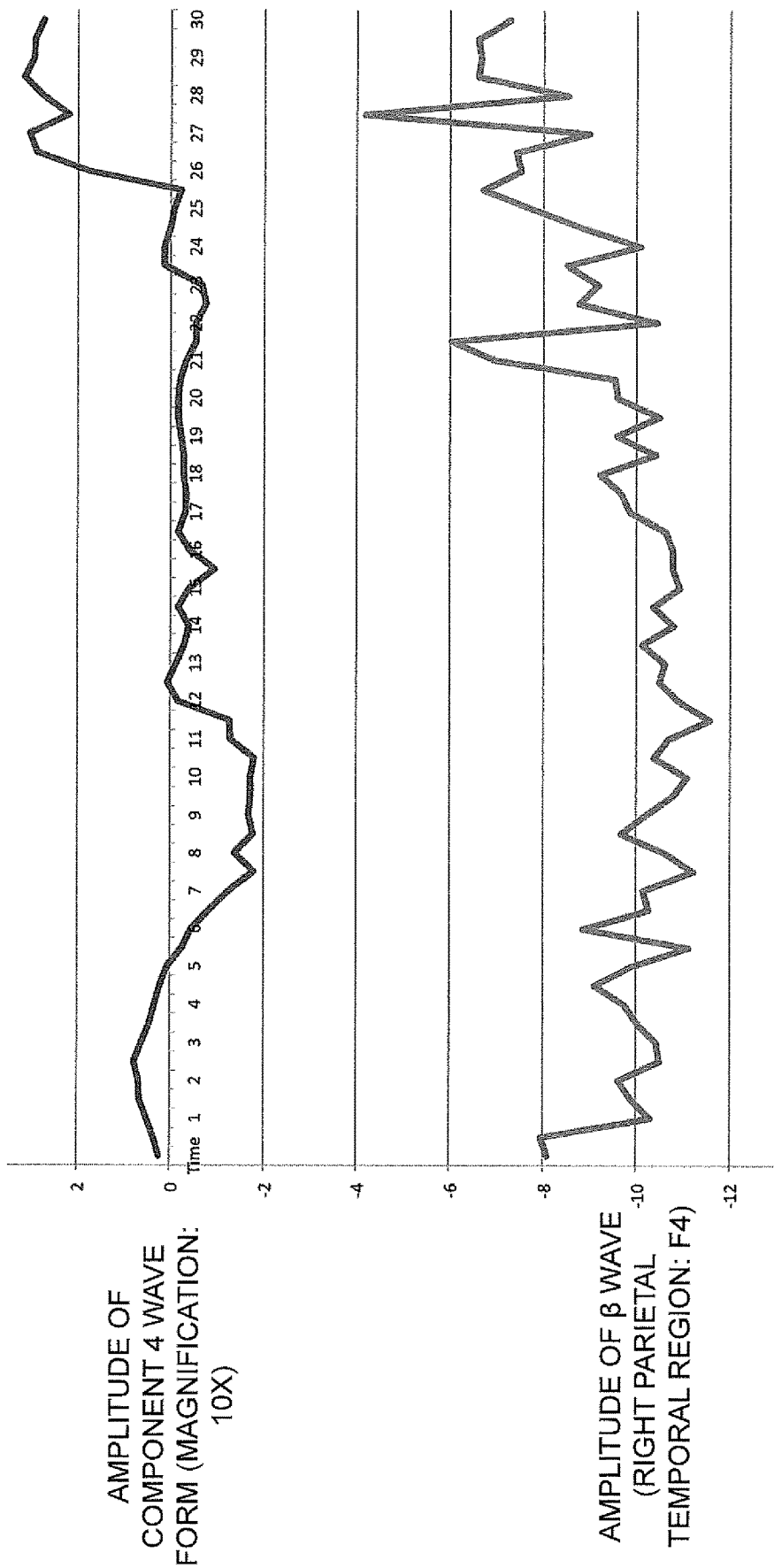
FIG. 11 is a chart illustrating a component waveform based on photographic image data of the facial surface, and the amplitude of the β wave of the measured brain waves.
Figure 12:
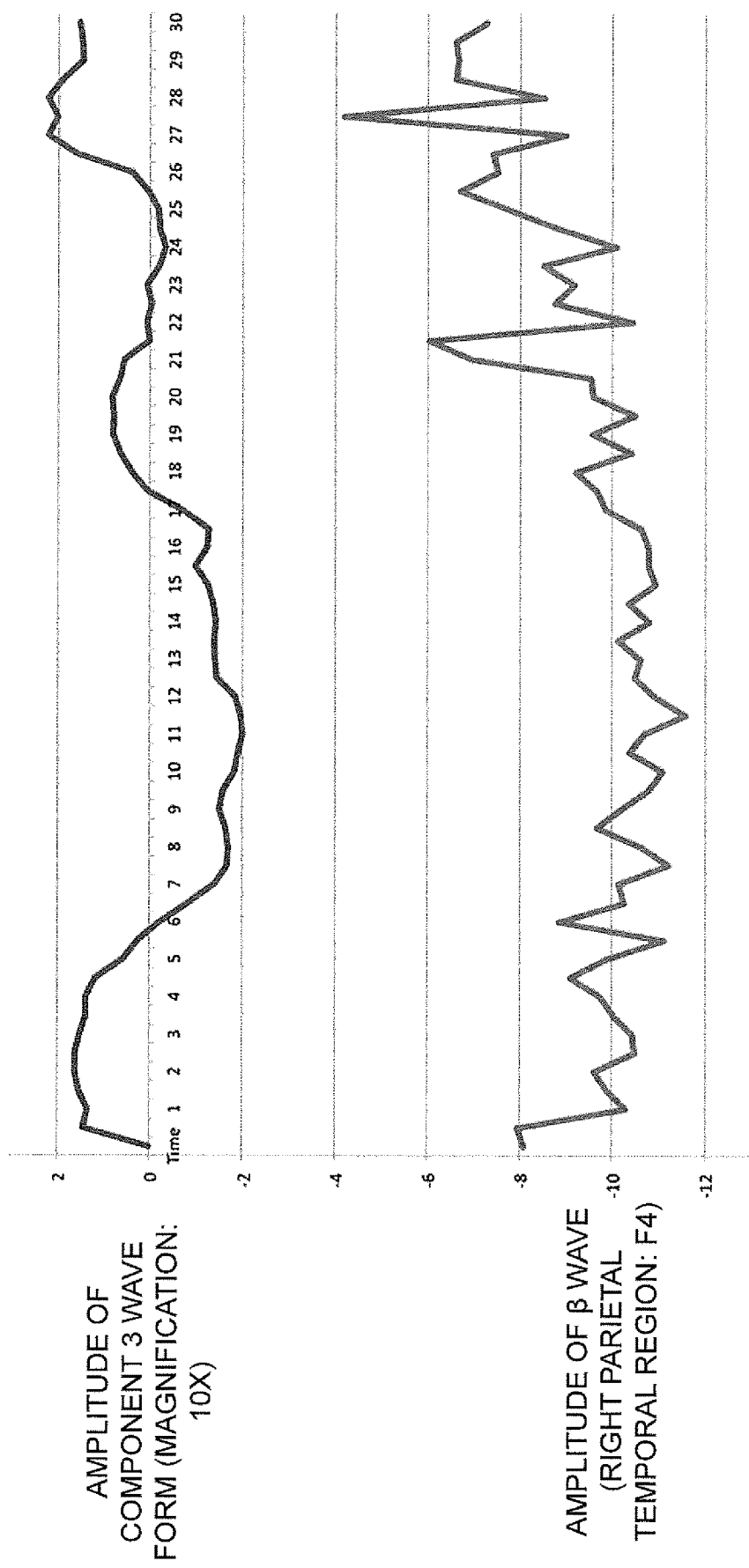
FIG. 12 is a chart illustrating a component waveform based on facial skin temperature data, and the amplitude of the β wave of the measured brain waves.
Figure 13:
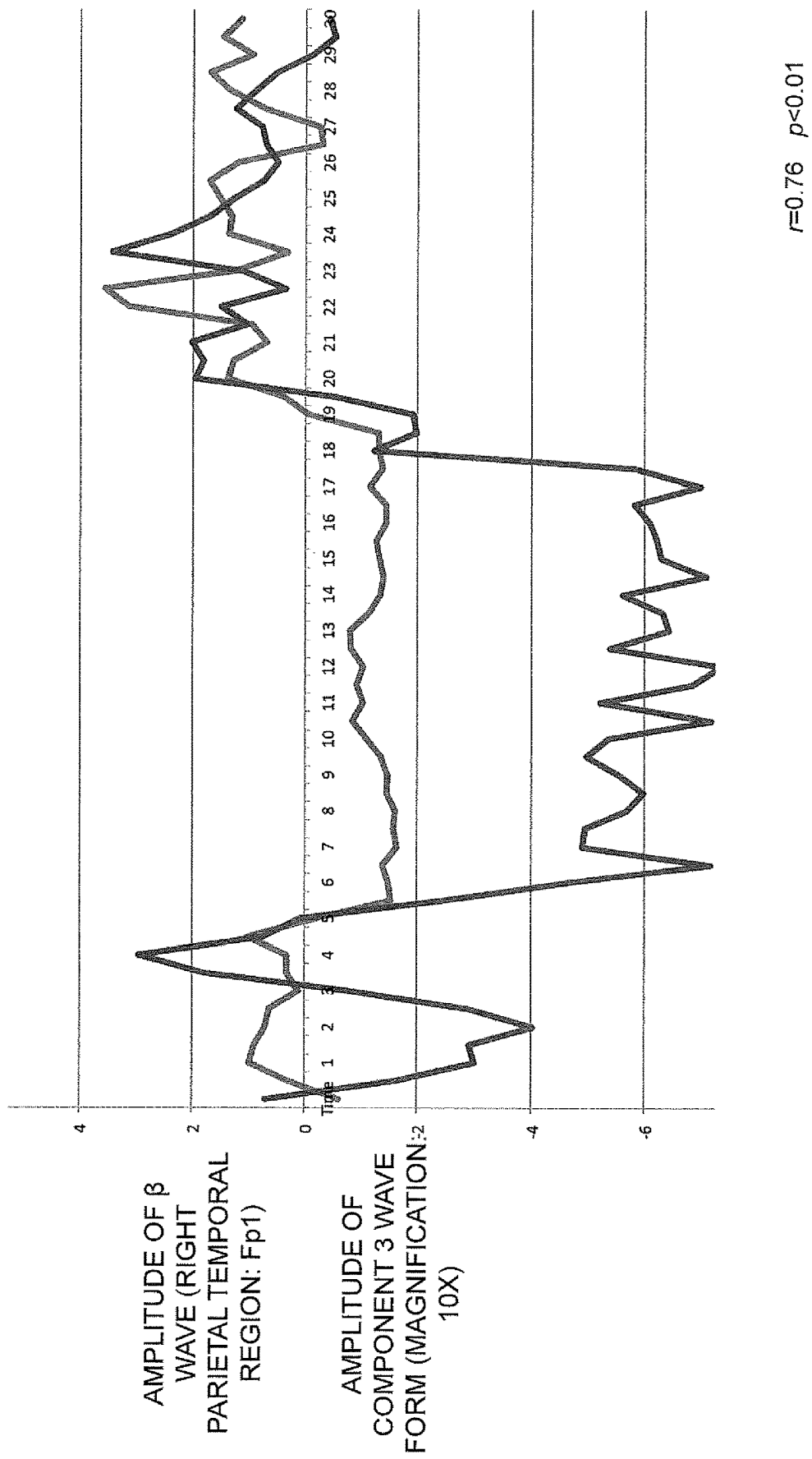
FIG. 13 is a chart illustrating a component waveform based on photographic image data of the facial surface, and the amplitude of the β wave of the measured brain waves.
Figure 14:
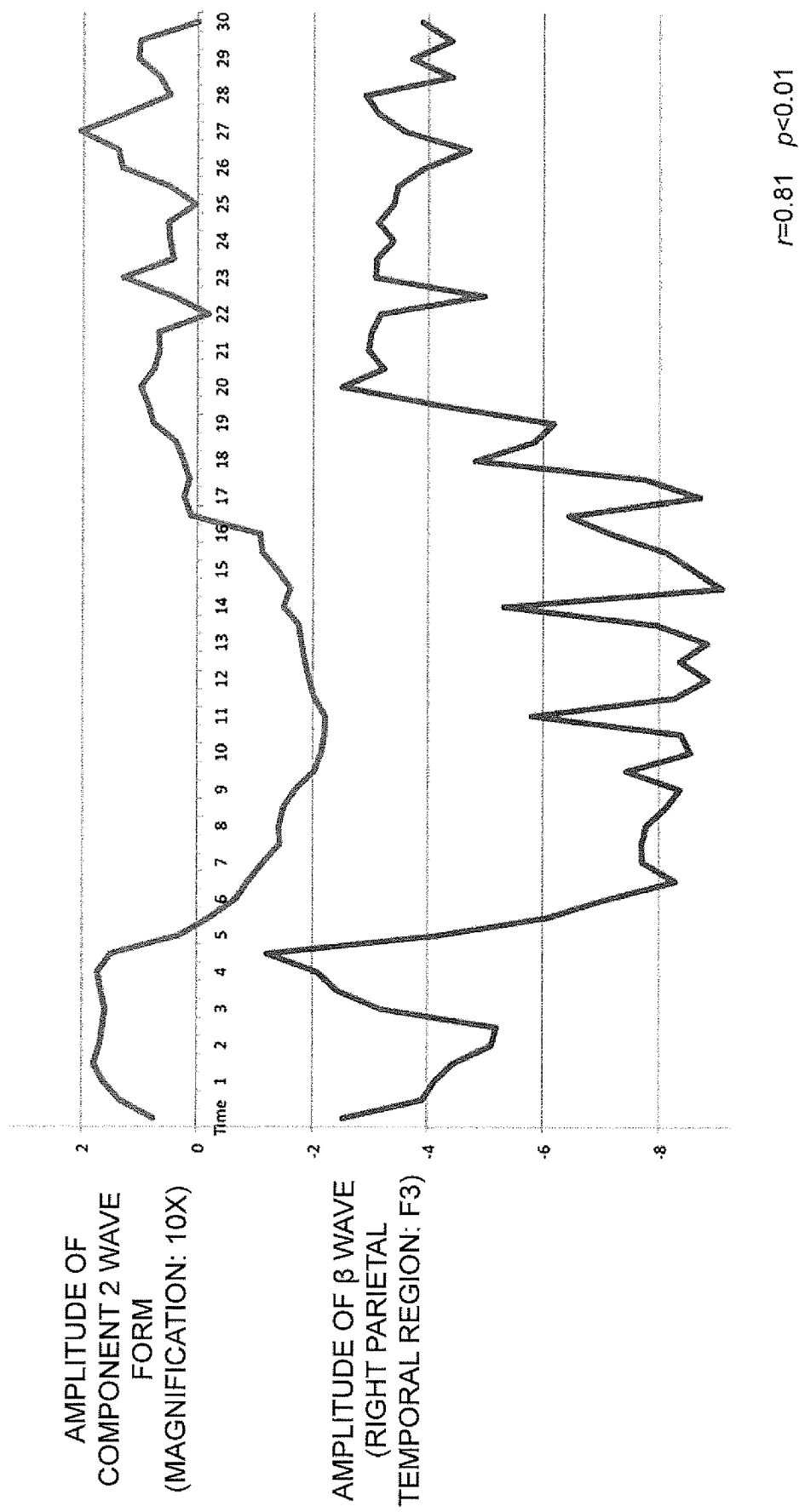
FIG. 14 is a chart illustrating a component waveform based on facial skin temperature data, and the amplitude of the β wave of the measured brain waves.
Figure 15:
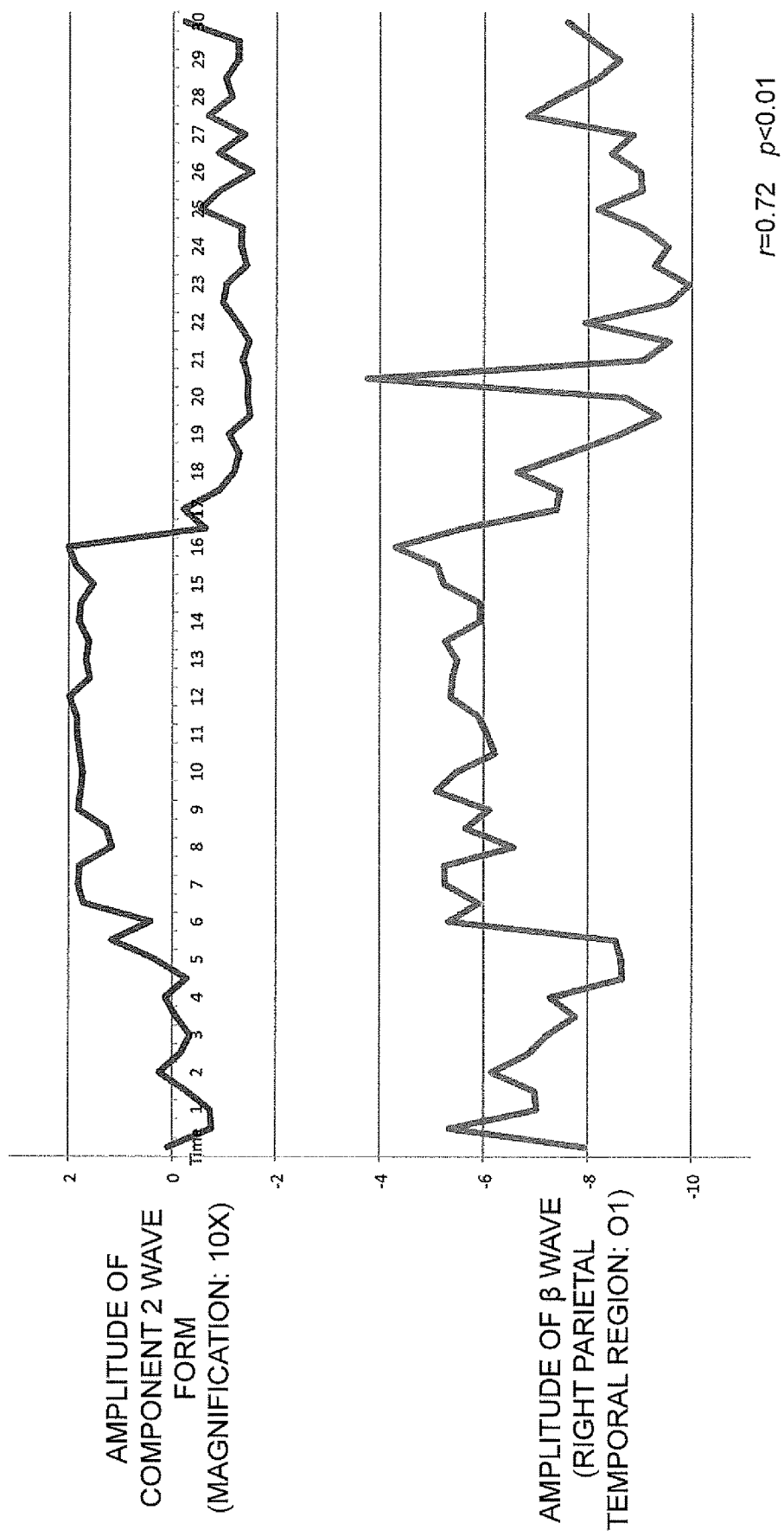
FIG. 15 is a chart illustrating a component waveform based on photographic image data of the facial surface, and the amplitude of the β wave of the measured brain waves.
Figure 16:
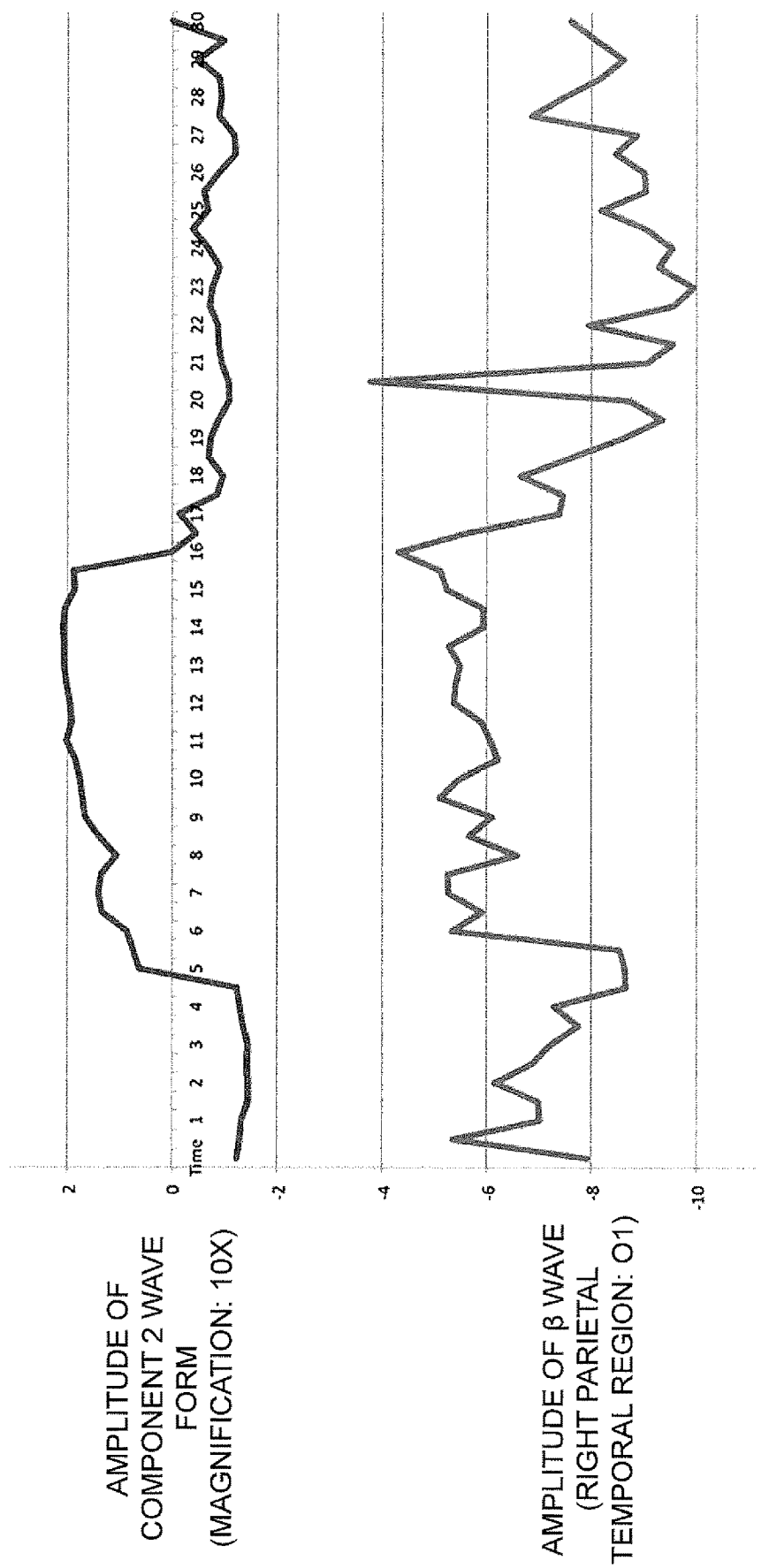
FIG. 16 is a chart illustrating a component waveform based on facial skin temperature data, and the amplitude of the β wave of the measured brain waves.
Figure 17:
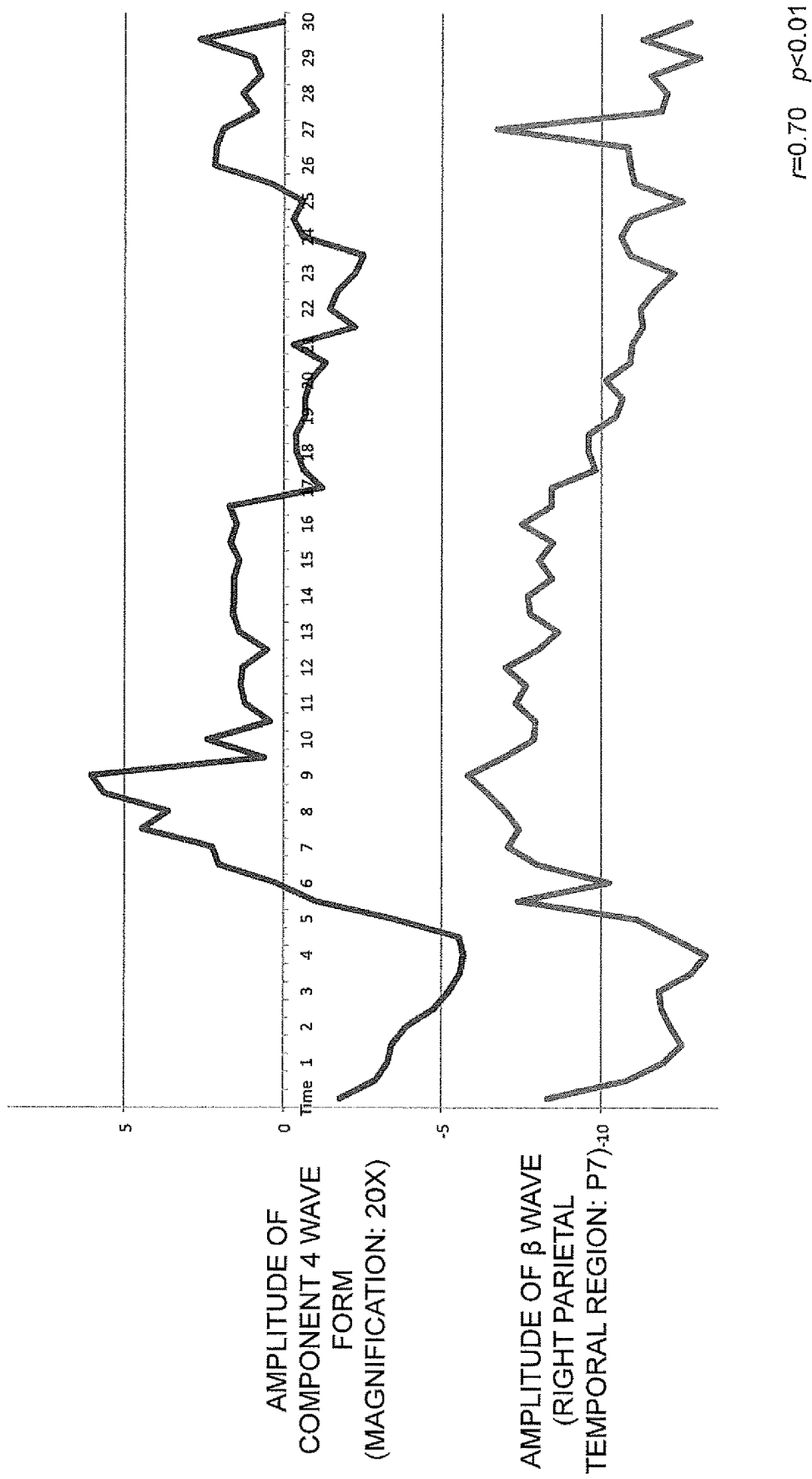
FIG. 17 is a chart illustrating a component waveform based on photographic image data of the facial surface, and the amplitude of the β wave of the measured brain waves.
Figure 18:
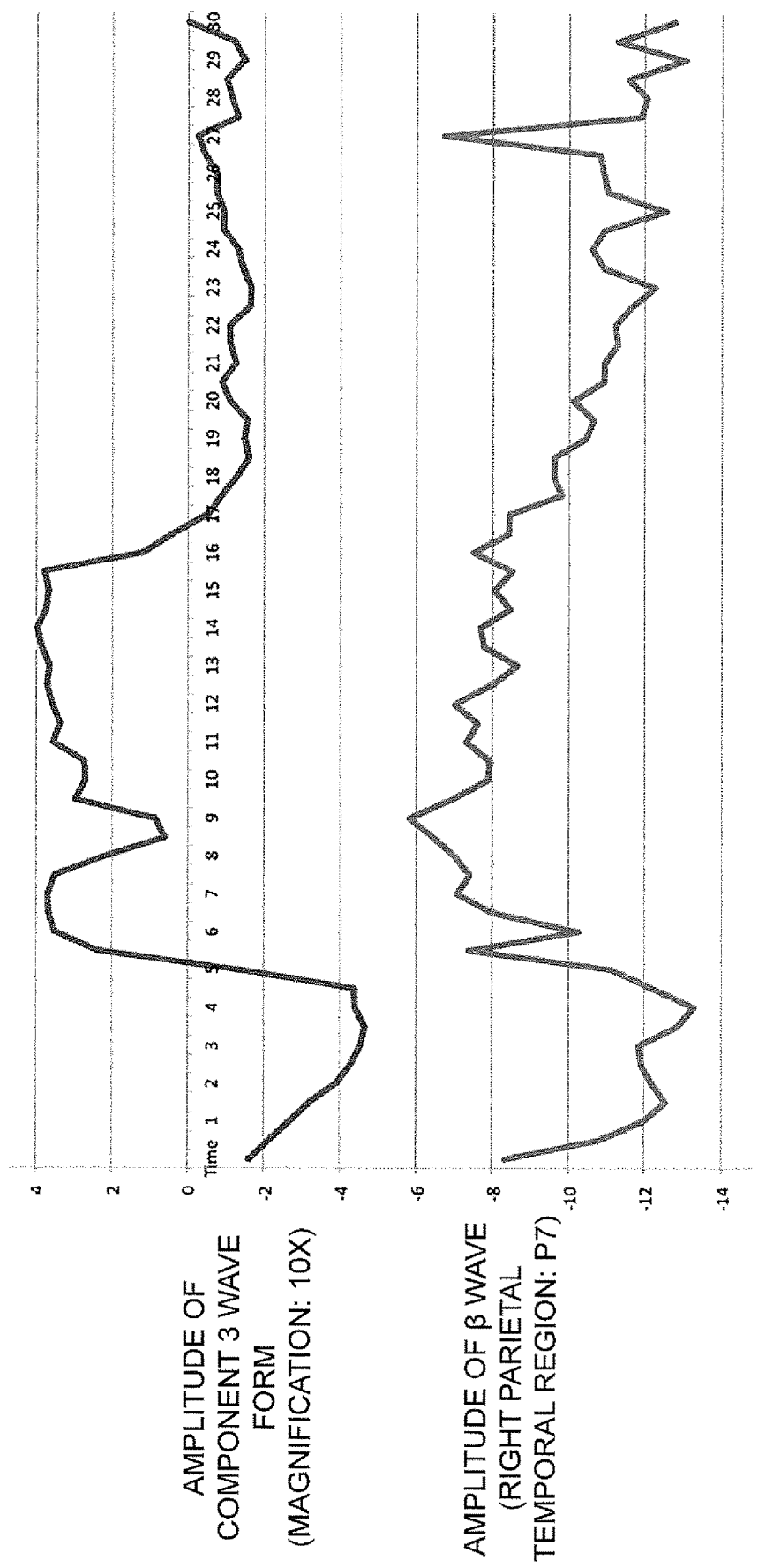
FIG. 18 is a chart illustrating a component waveform based on facial skin temperature data, and the amplitude of the β wave of the measured brain waves.

As illustrated in FIGS. 4 and 5, from the results of analyzing the brain waves, significant correlation was found the photographic image data of a subject 2, and the amplitude of the β wave of the measured brain waves of the subject 2. FIG. 10 illustrates the amplitude of the component waveform of the component 2 based on the facial skin temperature data of the subject 2, and the amplitude of the β wave of the measured brain waves of the subject 2. FIG. 11 illustrates the amplitude of the component waveform of a component 4 based on the photographic image data of a subject 3, and the amplitude of the β wave of the measured brain waves of the subject 3. FIG. 12 illustrates the amplitude of the component waveform of the component 3 based on the facial skin temperature data of the subject 3, and the amplitude of the β wave of the measured brain waves of the subject 3. FIG. 13 illustrates the amplitude of the component waveform of the component 3 based on the photographic image data of a subject 4, and the amplitude of the β wave of the measured brain waves of the subject 4. FIG. 14 illustrates the amplitude of the component waveform of the component 2 based on the facial skin temperature data of the subject 4, and the amplitude of the β wave of the measured brain waves of the subject 4. FIG. 15 illustrates the amplitude of the component waveform of the component 2 based on the photographic image data of the subject 5, and the amplitude of the β wave of the measured brain waves of the subject 5. FIG. 16 illustrates the amplitude of the component waveform of the component 2 based on the facial skin temperature data of the subject 5, and the amplitude of the β wave of the measured brain waves of the subject 5. FIG. 17 illustrates the amplitude of the component waveform of a component 4 based on the photographic image data of a subject 6, and the amplitude of the β wave of the measured brain waves of the subject 6. FIG. 18 illustrates the amplitude of the component waveform of the component 3 based on the facial skin temperature data of the subject 6, and the amplitude of the β wave of the measured brain waves of the subject 6.

As illustrated in FIGS. 7 to 18, from the results of the component waveforms and brain wave analyses, correlation was found between the facial skin temperature and the facial blood circulation volume. In each of the analyses based on the facial skin temperature data and the facial blood circulation volume data, significant correlation was found between the amplitude of each component waveform and the amplitude of the β wave measured by the electrodes attached to the top or back of the head.

Table 2 shows the results of analyzing the photographic image data of the facial surface of each subject.

TABLE 2

| Subject | Correlation in Blood Circulation Volume Data | | Correlation in Relative Conversion Blood Circulation Volume Data | |
|---|---|---|---|---|
| | Component waveform | Blood circulation volume distribution | Component waveform | Blood circulation Volume distribution |
| Subject 1 | Component 2 | 0.72 | Component 1 | 0.59 |
| | | | Component 2 | 0.85 |
| Subject 2 | Component 1 | 0.82 | Component 1 | 0.62 |
| | Component 2 | 0.82 | Component 2 | 0.60 |
| Subject 3 | Component 2 | 0.33 | Component 2 | 0.45 |
| | | | Component 3 | 0.56 |
| | Component 3 | 0.31 | Component 4 | 0.56 |
| Subject 4 | Component 1 | 0.57 | Component 1 | 0.66 |
| | Component 3 | 0.71 | Component 3 | 0.65 |
| Subject 5 | Component 1 | 0.56 | Component 1 | 0.51 |
| | Component 2 | 0.72 | Component 2 | 0.83 |
| Subject 6 | Component 2 | 0.38 | Component 2 | 0.45 |
| | | | Component 3 | 0.51 |
| | Component 4 | 0.68 | Component 5 | 0.36 |

As shown in Table 2, from the results obtained by analyzing the photographic image data of the facial surface described above, significant correlation was found between human brain activity and the components 1, 2, 3, 4, and 5 of the plurality of components obtained by decomposing the time-series blood circulation volume data based on the photographic image data of the facial surface by singular value decomposition. Note that, in this case, the components found to have significant correlation based on the blood circulation volume data and significant correlation based on the relative conversion blood circulation volume data were determined to have the significant correlation with human brain activity and, in addition, the components that did not have significant correlation based on the blood circulation volume data but did have significant correlation based on the relative conversion blood circulation volume data were also determined to have the significant correlation with human brain activity.

Table 3 shows the results of the control test.

TABLE 3

| | |
|---|---|
| Components having correlation with brain resting time/brain activated time | Component 1, Component 2 |
| Components having correlation with movement distance of face | Component 1, Component 3, Component 4 |
| Components having correlation with number of keyboard inputs | Component 8 |

As shown in Table 3, in the control test, when the subject moved while the photographic image data of the facial surface was being acquired, some of the components were found to have significant correlation between the amplitude of the component waveform thereof and each of the brain resting time and the brain activated time. Among these components, the component 2 was not found to have significant correlation with movement distance or the number of keyboard inputs. As such, it was confirmed that, among the plurality of components that were obtained by conducting the singular value decomposition the blood circulation volume data based on the RGB data acquired from the photographic image data of the facial surface a component having significant correlation with brain activity could be influenced by the movement of the subject while acquiring the time-series photographic image data of the facial surface, but this influence was much smaller than the influence resulting from the brain activity (the influence resulting from the activation or resting of the brain).

Based on these results, the present inventors made the following findings.

The blood circulation volume data, obtained from the RGB data of the facial surface based on time-series photographic image data of the facial surface acquired from the subjects, was decomposed into the plurality of components by singular value decomposition. As a result of analyzing each of the decomposed components, it was found that the components 1, 2, 3, 4, and 5 of the plurality of components are components that are related to brain activity. Specifically, it was found that it is possible to identify a component indicating an RGB change in the facial surface that reflects brain activity from the plurality of components, by decomposing the blood circulation volume data, which was obtained from the RGB data of the facial surface based on the time-series photographic image data of the facial surface into the plurality of components, extracting components having correlation with the activation/resting of the brain from the decomposed plurality of components, and analyzing the extracted components. Thus, the present inventors found that it is possible to estimate brain activity on the basis of time-series photographic image data of a human facial surface.

(4) Evaluation Device

Next, evaluation devices 10, 110 according to an embodiment of the present invention will be described. The evaluation devices 10, 110 were conceived by the inventor on the basis of the findings described above. The evaluation devices according to the present invention should not be construed as being limited to the following embodiments, and various types of modifications may be made without departing from the spirit or scope of the general inventive concept of the present invention.

The evaluation devices 10, 110 according to the embodiment of the present invention include brain activity estimation means 30 that estimate brain activity on the basis of facial skin temperature data, and/or brain activity estimation means 130 that estimate brain activity on the basis of photographic image data of the facial surface. Before describing the evaluation devices 10, 110 according to the embodiment of the present invention, each of the brain activity estimation means 30, 130 will be described.

Figure 19:
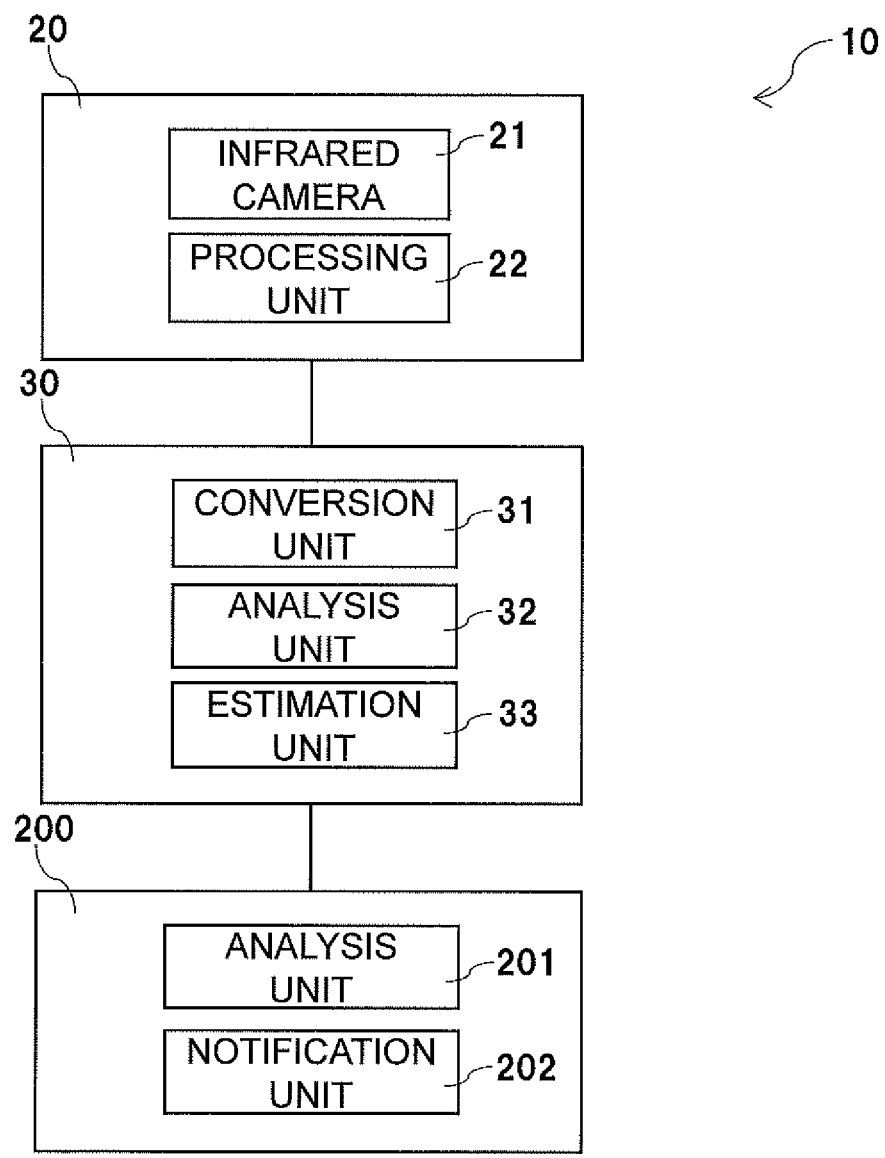
FIG. 19 is a schematic drawing of an evaluation device according to an embodiment of the present invention.
Figure 20:
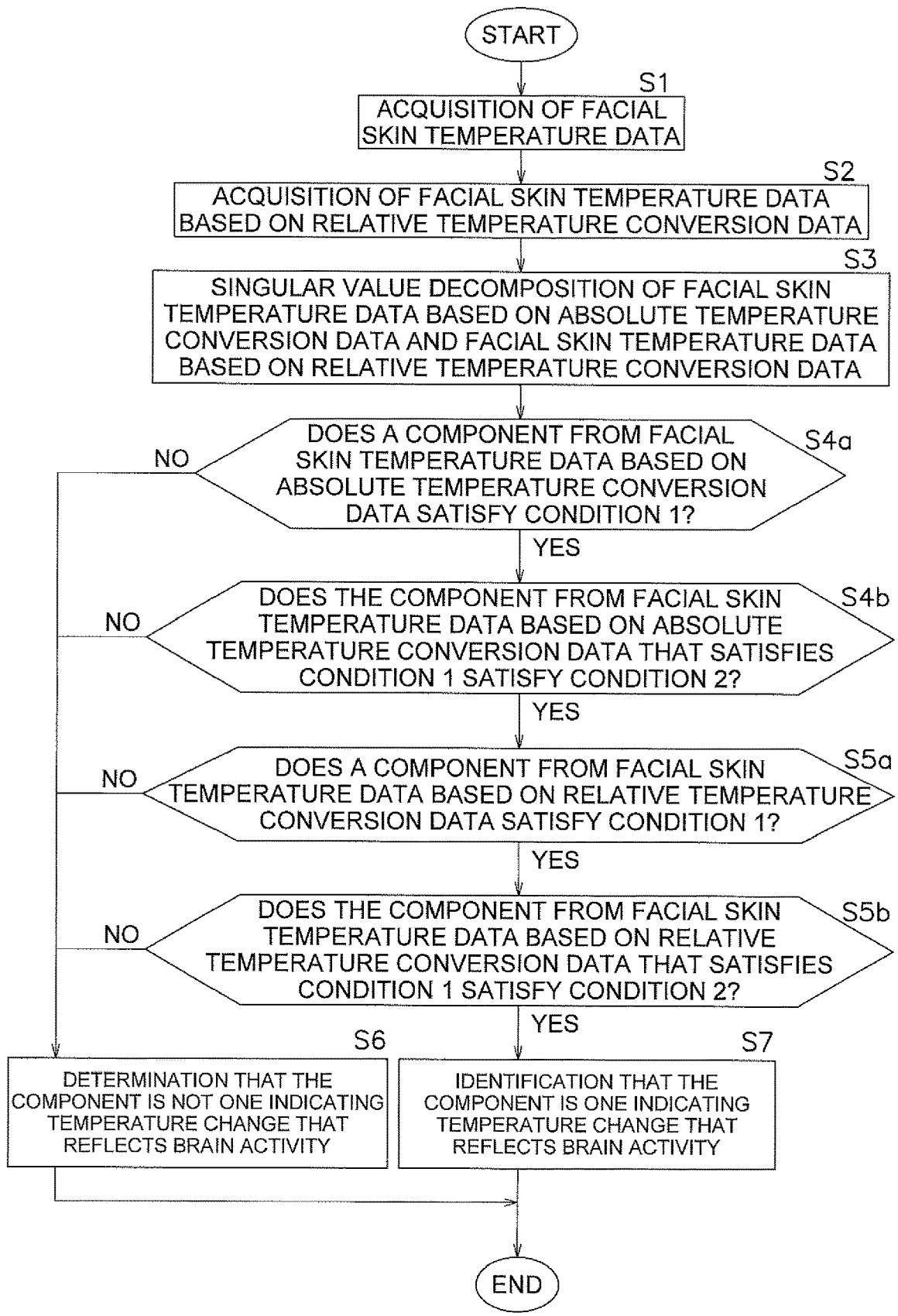
FIG. 20 is a flowchart showing an example of the flow of processing conducted in the evaluation device to identify a component indicating a change in skin temperature that reflects brain function.

(4-1) Brain Activity Estimation Means 30 that Estimate Brain Activity on the Basis of Facial Skin Temperature Data FIG. 19 is a schematic drawing of the evaluation device 10 according to an embodiment of the present invention. FIG. 20 is a flowchart showing the flow of processing conducted in the evaluation device 10 to identify a component indicating a change in skin temperature that reflects brain function.

The brain activity estimation means 30 of the evaluation device 10 estimate the brain activity of an individual (subject) from the facial skin temperature of the individual. As illustrated in FIG. 19, the evaluation device 10 includes facial skin temperature acquisition means 20, the brain activity estimation means 30, and evaluation means 200.

The facial skin temperature acquisition means 20 detect the skin temperature of at least a portion of the facial surface of the individual, and acquire facial skin temperature data including detected temperature data and position data of the detection site in time-series (step S1). Note that, in this case, the facial skin temperature acquisition means 20 is an infrared thermography device and includes an infrared camera 21 and a processing unit 22 as illustrated in FIG. 19. The infrared camera 21 is configured to detect infrared radiant energy emitted from the facial surface of the individual. Moreover, in this case, the infrared camera 21 is configured to detect infrared radiant energy emitted from the entire facial surface of the individual. The processing unit 22 converts the infrared radiant energy detected by the infrared camera 21 to temperatures to create temperature data. The processing unit 21 generates a temperature distribution diagram of the facial skin temperature of the entire facial surface, for which the sites where the infrared radiant energy was detected are used as the position data (coordinate data). The processing unit 21 processes the generated temperature distribution diagram as facial skin temperature data based on temperature conversion data. The processing unit 22 has a storage unit (not illustrated in the drawings) and the facial skin temperature data based on temperature conversion data is stored in this storage unit.

An example is described in which the temperature distribution diagram of the facial skin temperature of the whole facial surface is generated in the processing unit 22, but the present invention is not limited thereto. For example, a configuration is possible in which a temperature distribution diagram of facial skin temperature including at least the forehead and/or the area around the paranasal sinuses is generated and used as the facial skin temperature data based on temperature conversion data.

Additionally, in this case, a brain function activation task is given to the individual for a set period of time while the facial skin temperature acquisition means 20 are acquiring the facial skin temperature data based on temperature conversion data. That is, the facial skin temperature data based on temperature conversion data, acquired by the facial skin temperature acquisition means 20, contains data for a period in which the brain function activation task was being given to the individual. Note that the brain function activation task given to the individual is not particularly limited provided that the task is presumed to place the brain in an activated state, and the content thereof may be appropriately determined in accordance with the purpose of use of the evaluation device 10.

The brain activity estimation means 30 estimate human brain activity on the basis of facial skin temperature data based on the temperature conversion data acquired by the facial skin temperature acquisition means 20. Specifically, the brain activity estimation means 30 include a conversion unit 31, an analysis unit 32, and an estimation unit 33 as illustrated in FIG. 19.

The conversion unit 31 converts the temperature data included in the facial skin temperature data based on temperature conversion data to relative temperature data, and generates facial skin temperature data based on the converted relative temperature data, that is, facial skin temperature data based on relative temperature conversion data (step S2). Specifically, the conversion unit 31 uses, as a reference, an average of the temperature data included in the facial skin temperature data based on temperature conversion data for every predetermined time period (e.g. 30 seconds), and converts the temperature data to relative temperature data. Then, the conversion unit 31 uses the converted relative temperature data and the position data to generate the facial skin temperature data based on relative temperature conversion data.

The analysis unit 32 decomposes each of the time-series facial skin temperature data based on temperature conversion data and the facial skin temperature data based on relative temperature conversion data into a plurality of components by singular value decomposition, principal component analysis, or independent component analysis (step S3). Here, the analysis unit 32 subjects each of the acquired facial skin temperature data based on temperature conversion data and the facial skin temperature data based on relative temperature conversion data to singular value decomposition in which the SVD of MATLAB (registered trademark) is used as the analysis tool. In the singular value decomposition, for each of the acquired facial skin temperature data in time-series based on temperature conversion data and the facial skin temperature data based on relative temperature conversion data, the factor is set to time data per predetermined time period (e.g. 30 seconds), and the measure is set to the facial skin temperature data based on temperature conversion data and the facial skin temperature data based on relative temperature conversion data in each time period. Then, the facial skin temperature data based on temperature conversion data and the facial skin temperature data based on relative temperature conversion data are each decomposed into a plurality of components by singular value decomposition. Thereafter, the analysis unit 32 calculates a time distribution, a space distribution, and a singular value representing the magnitude of each component.

Additionally, the analysis unit 32 determines whether or not each component satisfies a first condition and a second condition in order to identify a component, from the plurality of components decomposed by singular value decomposition, indicating a change in skin temperature that reflects brain activity (step S4a, step S4b, step S5a, and step S5b). Note that, in this case, the analysis unit 32 first determines whether or not each component from the facial skin temperature data based on temperature conversion data satisfies the first condition (step S4a). Then, for components from the facial skin temperature data based on temperature conversion data determined to satisfy the first condition in step S4a, the analysis unit 32 determines whether or not those components satisfy the second condition (step S4b). Then, the analysis unit 32 determines whether or not each component from the facial skin temperature data based on relative temperature conversion data, matching the components determined to satisfy the first condition and the second condition in step S4a and step S4b, satisfies the first condition (step S5a). Then, the analysis unit 32 determines whether or not the components from the facial skin temperature data based on relative temperature conversion data, which is determined to satisfy the first condition in step S5a satisfy the second condition (step S5b). However, the order of determination in the analysis unit 32 is not limited thereto and, for example a configuration is possible in which it is determined whether or not the components from the facial skin temperature data based on temperature conversion data and the components from the facial skin temperature data based on relative temperature conversion data satisfy the first condition and the second condition respectively, and the components for which the determination results match are ultimately extracted.

The first condition is that the amplitude of the component waveform of the component decomposed by singular value decomposition has correlation with changes at brain resting time and brain activated time. The analysis unit 32 extracts, from the plurality of components, components satisfying the first condition as determination components. Note that, the brain function activation task is given to the individual for a set period of time while the facial skin temperature data based on temperature conversion data is being acquired. The brain resting time is defined as the period in which the brain function activation task is not being given to the individual, and the brain activated time is defined as the period in which the brain function activation task is being given to the individual. Here, the analysis unit 32 conducts a comparative analysis of the component waveform of each component against the periods in which the brain function activation task is and is not being given. Using the results of this comparative analysis based on the component waveform data, the analysis unit 32 evaluates whether or not there is correlation between the component waveform of each component and each of the brain resting time and the brain activated time. Then, the analysis unit 32 extracts, from the plurality of components, components evaluated as having correlation as a determination component that satisfies the first condition. Meanwhile, the analysis unit 32 determines that, among the plurality of components, a component evaluated as not having correlation is the component that does not satisfy the first condition and is not the component indicating a temperature change that reflects human brain activity (step S6).

In this case, the brain function activation task is given to the individual for a set period of time while acquiring the facial skin temperature data based on temperature conversion data, and the analysis unit 32 extracts the determination components based thereon. However, the content of the first condition, that is, the means of extracting the determination component by the analysis unit 32, is not limited thereto. For example, when the components, among the plurality of components, indicating a component waveform that has correlation with the brain resting time and the brain activated time are already identified by previous experiments or the like, the analysis unit 32 may extract these identified components from the plurality of components as the determination components. Additionally, with this evaluation device, in cases where human behavior, which is known to be related to the activation/resting of the brain such as eye movement and blinking are detected, the analysis unit 32 may extract the determination components from the plurality of components by comparing and analyzing the detection results against the component waveform of each component and conducting an evaluation. Note that the criterion for the analysis unit 32 to determine whether or not the first condition is satisfied is appropriately decided by simulations, experiments, theoretical calculations, or the like, in accordance with the purpose of use of the evaluation device 10 or the like.

The second condition is that there is a temperature change at the predetermined site on the human facial surface in the extracted determination components. The analysis unit 32 determines that, among the determination components, the components that satisfy the second condition have a high potential of being related to human brain activity, and extracts these as candidate components. That is, the analysis unit 32 determines whether or not the determination components are related to human brain activity on the basis of the presence/absence of a temperature change at the predetermined site on a human facial surface. Specifically, the analysis unit 32 determines whether or not temperature change has occurred at the forehead and/or the area around the paranasal sinuses on the basis of the temperature distribution data of the extracted determination components. When a temperature change has occurred, the analysis unit 32 determines that there is a high possibility that the determination component satisfies the second condition and is related to human brain activity, and extracts that determination component as a candidate component. Meanwhile, when a temperature change has not occurred at the forehead or the area around the paranasal sinuses, the analysis unit 32 determines that the determination component does not satisfy the second condition and is not a component indicating a skin temperature change that reflects human brain activity (step S6). Note that the criterion for the analysis unit 32 to determine whether or not the second condition is satisfied is appropriately decide by simulations, experiments, theoretical calculations, or the like, in accordance with the purpose of use of the evaluation device 10.

Then, the analysis unit 32 identifies the component which is determined to satisfy the second condition in step S5b, as a component indicating a change in skin temperature that reflects brain activity (step S7). That is, the component identified in step S7 as the component indicating a change in skin temperature that reflects brain activity is a component that is present in both the candidate components extracted by decomposing and analyzing the facial skin temperature data based on temperature conversion data by singular value decomposition and the candidate components extracted by decomposing and analyzing the facial skin temperature data based on relative temperature conversion data by singular value decomposition. Note that, the candidate components for which both analyses do not match are determined that they are not the components indicating a change in skin temperature that reflects brain activity in step S6.

The estimation unit 33 estimates human brain activity on the basis of the component identified by the analysis unit 32 as a component indicating a change in skin temperature that reflects human brain activity. Specifically, the estimation unit 33 estimates an amount of brain activity when acquiring the facial skin temperature data on the basis of the component waveform data of the component identified by the analysis unit 32.

(4-1-1) Modification Example 1A

The brain activity estimation means 30 described above includes the conversion unit 31, and the facial skin temperature data based on relative temperature conversion data is generated by the conversion unit 31. Moreover, the analysis unit 32 uses singular value decomposition to decompose, into a plurality of components, not only the facial skin temperature data based on temperature conversion data acquired by the facial skin temperature acquisition means 20, but also the facial skin temperature data based on relative temperature conversion data, which is from the temperature data that has been converted into relative temperature data. Then, the analysis unit 32 analyzes each of the components.

Instead of this, a configuration in which the brain activity estimation means 30 does not include the conversion unit 31 can be adopted. In this case, the processes for generating the facial skin temperature data based on relative temperature conversion data and analyzing the data from the facial skin temperature data based on relative temperature conversion data can be omitted.

However, in order to accurately identify the component related to human brain activity, it is preferable that the brain activity estimation means 30 include the conversion unit 31, as in the embodiment described above. Moreover, it is preferable that the analysis unit 32 conducts singular value decomposition to decompose, into a plurality of components, not only the facial skin temperature data based on temperature conversion data acquired by the facial skin temperature acquisition means 20, but also the facial skin temperature data based on relative temperature conversion data, which is from the temperature data that has been converted into relative temperature data; and analyzes each of the components.

(4-1-2) Modification Example 1B

The facial skin temperature acquisition means 20 described above is an infrared thermography device capable of acquiring temperature data in a state of non-contact with the subject.

However, the facial skin temperature acquisition means are not particularly limited to an infrared thermography device, provided that the facial skin temperature acquisition means are capable of detecting the skin temperature of at least a portion of the facial surface of the individual, and acquiring facial skin temperature data including detected temperature data and position data of the detection site in time-series.

For example, the facial skin temperature acquisition means may be a device that includes temperature sensors. Specifically, a configuration is possible in which the temperature sensors are applied to predetermined sites on the facial surface of the individual, and the time-series facial skin temperature data is acquired on the basis of temperature data detected by the temperature sensors and the position data of the sites where the temperature sensors are applied. Even in cases where the facial skin temperature data is acquired while the temperature sensors are in contact with the individual, namely the subject, there is no need to treat the temperature sensors prior to application, unlike cases in which electroencephalogram electrodes or the like are used. As a result, data can be acquired more easily compared to conventional detection methods such as electroencephalography, functional magnetic resonance imaging, and near infrared spectroscopy. As such, human brain activity can be easily estimated.

Figure 21:
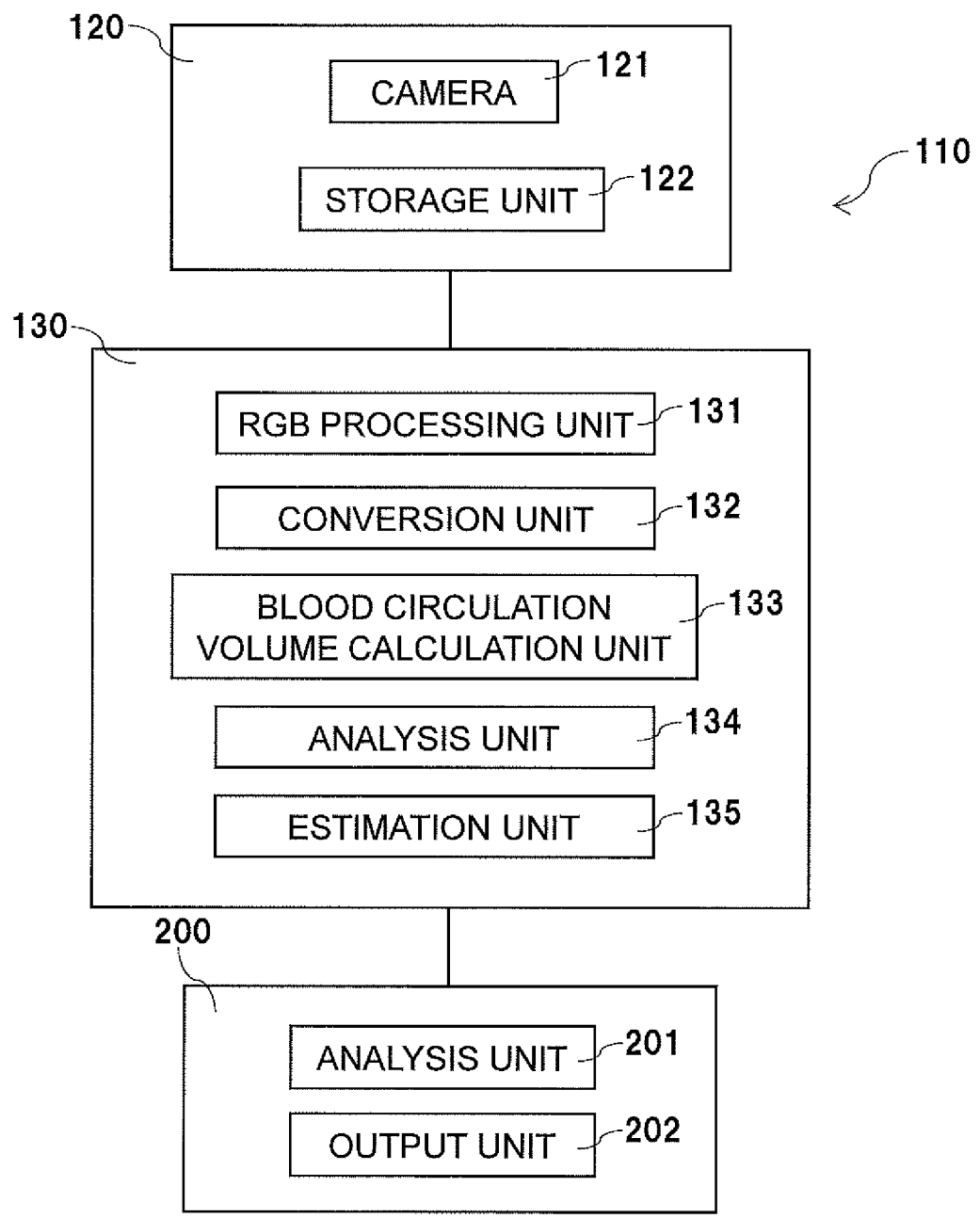
FIG. 21 is a schematic drawing of the evaluation device according to an embodiment of the present invention.
Figure 22:
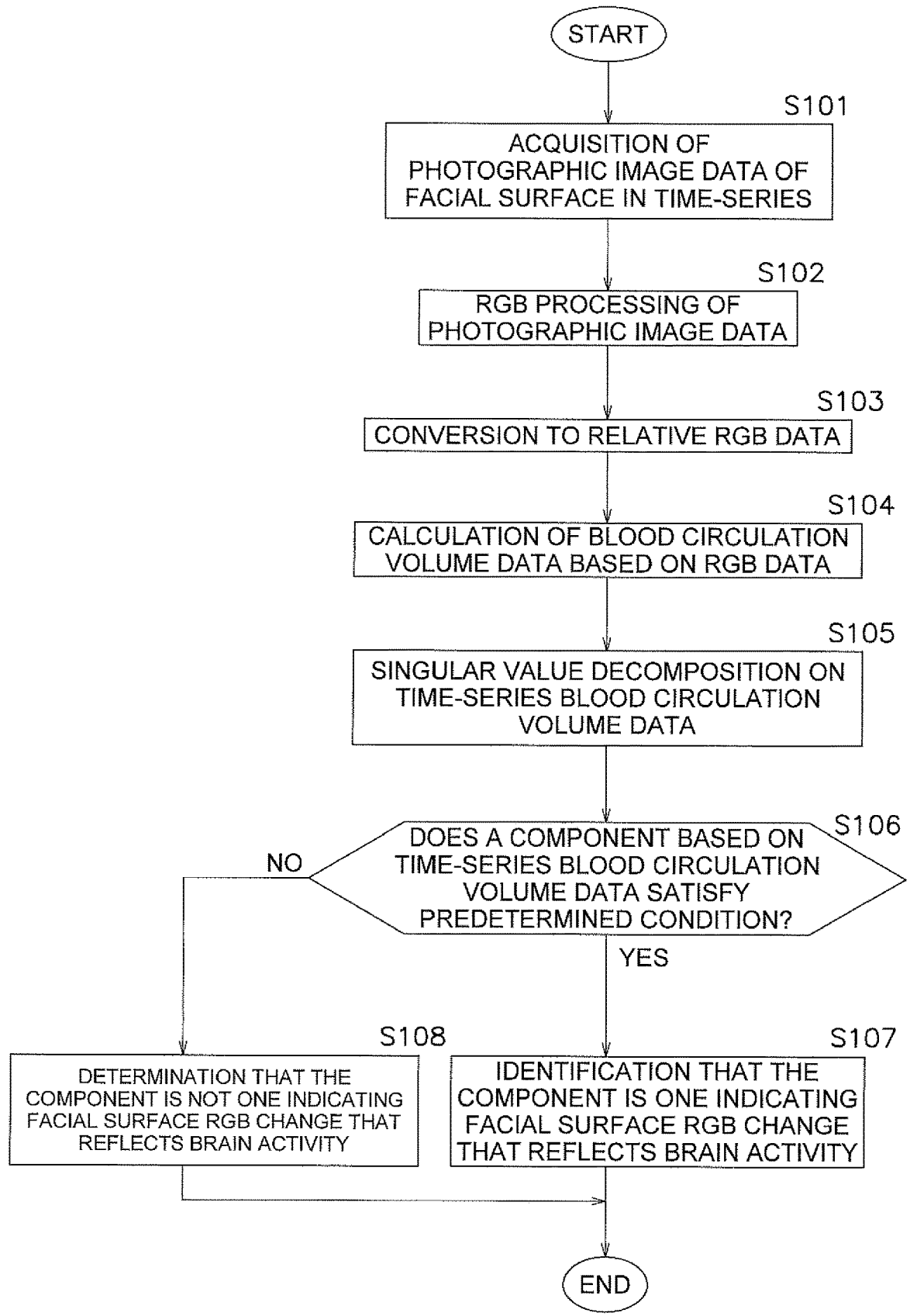
FIG. 22 is a flowchart showing an example of the flow of processing conducted in the evaluation device to identify a component indicating an RGB change in the facial surface that reflects brain function.

(4-2) Brain Activity Estimation Means 130 that Estimate Brain Activity on the Basis of Photographic Image Data of Facial Surface FIG. 21 is a schematic drawing of the evaluation device 110 according to an embodiment of the present invention. FIG. 22 is a flowchart showing an example of the flow of processing conducted in the evaluation device 110 to identify a component indicating an RGB change in the facial surface that reflects brain function.

The brain activity estimation means 130 of the evaluation device 110 estimate the brain activity of an individual (subject) from the photographic image data of the facial surface of the individual. As illustrated in FIG. 21, the evaluation device 110 includes image data acquisition means 120, brain activity estimation means 130, and evaluation means 200.

The image data acquisition means 120 acquire photographic image data of at least a portion of the facial surface of the individual in time-series (step S101). Note that the image data acquisition means 120 are not particularly limited provided that they at least include an imaging device, and examples thereof include smartphones, tablets (e.g. iPad (registered trademark)), and other portable terminals with built in imaging devices. In this case, as illustrated in FIG. 21, the image data acquisition means 120 include a storage unit 122 and a camera 121 as the imaging device. The camera 121 is configured to acquire photographic image data of the facial surface of the individual in time-series. In this case, the camera 121 captures video of the entire facial surface of the individual and acquires the captured video data. The time-series photographic image data captured by the imaging device is stored in the storage unit 122. In this case, the video data acquired by the camera 121 is stored in the storage unit 122.

Note that, in this case, the camera 121 captures video of the entire facial surface, but the present invention is not limited thereto. For example, a configuration is possible in which the camera 121 captures video including images of at least the forehead and/or the area around the paranasal sinuses of the face.

Additionally, in this case, the brain function activation task is given to the individual for a set period of time while the image data acquisition means 120 are acquiring the time-series photographic image data of the facial surface. That is, the photographic image data acquired by the image data acquisition means 120 contains data for a period in which the brain function activation task is being given to the individual. Note that the brain function activation task given to the individual is not particularly limited provided that the task is presumed to place the brain in an activated state, and the content thereof may be appropriately determined in accordance with the purpose of use of the evaluation device 110.

The brain activity estimation means 130 estimate human brain activity on the basis of the time-series photographic image data on the facial surface acquired by the image data acquisition means 120. Specifically, the brain activity estimation means 130 include an RGB processing unit 131, a conversion unit 132, a blood circulation volume calculation unit 133, an analysis unit 134, and an estimation unit 135 as illustrated in FIG. 21. Note that, in FIG. 21, a configuration is illustrated in which the brain activity estimation means 130 are a single device including the RGB processing unit 131, the conversion unit 132, the blood circulation volume calculation unit 133, the analysis unit 134, and the estimation unit 135. However, the present invention is not limited thereto and configurations are possible in which some or all of the RGB processing unit 131, the conversion unit 132, the blood circulation volume calculation unit 133, the analysis unit 134, and the estimation unit 135 are provided as independent devices. Additionally, in this case, facial blood circulation volume acquisition means are configured from the image data acquisition means 120, the RGB processing unit 131, the conversion unit 132, and the blood circulation volume calculation unit 133.

The RGB processing unit 131 performs RGB processing on the photographic image data acquired by the image data acquisition means 120 to decompose the photographic image data into three color components, namely an R component, a G component, and a B component (step S102). The RGB processing may be performed on the photographic image data of the entire facial surface but, in this case, the data of the forehead and/or area around the paranasal sinuses is extracted from the photographic image data and the RGB processing is performed on the extracted data in order to reduce computation load and noise.

The conversion unit 132 converts RGB data of the photographic image data obtained by the RGB processing to relative RGB data (step S103). Specifically, the conversion unit 132 uses, as a reference, an average of the RGB data obtained from the photographic image data for every predetermined time period (e.g. 30 seconds) to convert the RGB data to relative RGB data.

The blood circulation volume calculation unit 133 calculates time-series blood circulation volume data of the facial surface on the basis of the RGB data of the photographic image data obtained by the RGB processing (step S104).

The analysis unit 134 decomposes the time-series relative conversion blood circulation volume data into a plurality of components by singular value decomposition, principal component analysis, or independent component analysis (step S105). Here, the analysis unit 134 subjects each of the relative conversion blood circulation volume data to singular value decomposition in which the SVD of MATLAB (registered trademark) is used as the analysis tool. Specifically, in the singular value decomposition, for the time-series relative conversion blood circulation volume data, the factor is set to time data per predetermined time period (e.g. 30 seconds), and the measure is set to the relative conversion blood circulation volume data per pixel, as calculated from the relative RGB data at each time period. Then, the time-series relative conversion blood circulation volume data is decomposed into a plurality of components by singular value decomposition and a time distribution, a space distribution, and a singular value representing the magnitude of each component is calculated.

Additionally, the analysis unit 134 determines whether or not each component satisfies predetermined conditions in order to identify a component, from the plurality of components decomposed by the singular value decomposition, indicating an RGB change in the facial surface that reflects brain activity (step S106). The predetermined condition includes conditions such as, for example, that the amplitude of the component waveform of the component decomposed by singular value decomposition has correlation with changes at brain resting time and brain activated time (hereinafter referred to as "first condition"), and/or that there is a blood circulation volume change at a predetermined site on the human facial surface in the component decomposed by the singular value decomposition (hereinafter referred to as "second condition"). One or a plurality of conditions may be set as the predetermined condition determined by the analysis unit 134. In this case, the first condition is set as the predetermined condition.

Then, the analysis unit 134 extracts, from the plurality of components, a component that satisfies the predetermined condition as a determination component. Furthermore, the analysis unit 134 identifies, from the extracted determination components, components that satisfy all of the conditions included in the predetermined condition as components indicating an RGB change in the facial surface that reflects brain activity (step S107). Meanwhile, the analysis unit 134 determines that the components among the plurality of components that do not satisfy one or more of the conditions included in the predetermined condition are not components indicating an RGB change in the facial surface that reflects brain activity (step S108).

In this case, as described above, only one condition is set as the predetermined condition, and the brain function activation task is given to the individual for a set period of time while the time-series photographic image data is being acquired. Therefore, the brain resting time is defined as the period of time in which the brain function activation task is not being given to the individual, and the brain activated time is defined as the period of time in which the brain function activation task is being given to the individual. The analysis unit 134 conducts a comparative analysis of the component waveform of each component against the periods of time in which the brain function activation task is and is not being given. Using the results of this comparative analysis based on the component waveform data, the analysis unit 134 evaluates whether or not there is correlation between the component waveform of each component and each of the brain resting time and the brain activated time. Then, the analysis unit 32 extracts, from the plurality of components, a component evaluated as having correlation as a determination component that satisfies the predetermined condition. The analysis unit 134 identifies this determination component as a component indicating an RGB change in the facial surface that reflects brain activity. Meanwhile, the analysis unit 134 determines that, among the plurality of components, a component evaluated as not having correlation is the component that does not satisfy the predetermined condition, and is not the component indicating an RGB change in the facial surface that reflects human brain activity.

In this case, the brain function activation task is given to the individual for a set period of time while acquiring the time-series photographic image data of the facial surface, and the analysis unit 134 extracts the determination component on the basis thereof. However, the content of the first condition, that is, the means of extracting the determination component by the analysis unit 134, is not limited thereto. For example, when the component, among the plurality of components, indicating the component waveform that has correlation with the brain resting time and the brain activated time is already identified by previous experiments or the like, the analysis unit 134 extracts this identified component from the plurality of components as the determination component. Additionally, with the evaluation device 110, in cases where human behavior known to be related to the activation/resting of the brain such as eye movement and blinking are detected, the analysis unit 134 may extract the determination component from the plurality of components by comparing these detection results against the component waveform of each component and conducting an evaluation. Note that the criterion for the analysis unit 134 to determine whether or not the first condition is satisfied is appropriately determined by simulations, experiments, theoretical calculations, or the like, in accordance with the purpose of use of the evaluation device 110 or the like.

Additionally, in cases where the second condition is set as the predetermined condition, the analysis unit 134 extracts the determination component on the basis of the presence/absence of a change in facial blood circulation volume at the predetermined site on the human facial surface. Specifically, the analysis unit 134 determines whether or not a change in the blood circulation volume has occurred at the forehead and/or the area around the paranasal sinuses, on the basis of the blood circulation volume distribution diagrams corresponding to the plurality of components decomposed by singular value decomposition. When a change in the blood circulation volume has occurred, the analysis unit 32 determines that said component satisfies the second condition. Meanwhile, when a change in the blood circulation volume has not occurred at the forehead or the area around the paranasal sinuses, the analysis unit 32 determines that said component does not satisfy the second condition. Note that the criterion for the analysis unit 134 to determine whether or not the second condition is satisfied is appropriately determined by simulations, experiments, theoretical calculations, or the like, in accordance with the purpose of use of the evaluation device 110 or the like.

Furthermore, in cases where the blood circulation volume calculation unit 133 calculates the time-series blood circulation volume data based on the RGB data prior to being converted to the relative RGB data, a configuration is possible in which the analysis unit 134 determines whether or not the first condition and/or the second condition is satisfied and extracts a determination component from the plurality of components obtained by subjecting the blood circulation volume data to singular value decomposition or the like.

The estimation unit 135 estimates human brain activity on the basis of the component identified by the analysis unit 134 as a component indicating an RGB change in the facial surface that reflects human brain activity. Specifically, the estimation unit 135 estimates an amount of brain activity when acquiring the photographic image data of the facial surface, on the basis of the component waveform data of the component identified by the analysis unit 134.

(4-2-1) Modification Example 2A

As described above, smartphones, tablets (e.g. iPad (registered trademark)), and other portable terminals with built in imaging devices may be used as the camera 121. In other words, any device that captures images in the visible light region can be used for the photographic image data described above.

Additionally, in the blood circulation volume calculation unit 133, the blood circulation volume data of the facial surface may be calculated using mainly the R component of each pixel included in the RGB data. Provided that the blood circulation volume data can be calculated on the basis of the RGB data, the blood circulation volume data need not be limited to the erythema index.

(4-2-2) Modification Example 2B

The blood circulation volume calculation unit 133 described above calculates the relative conversion blood circulation volume data on the basis of relative RGB data converted by the conversion unit 132. However, in place of or in addition to this, the blood circulation volume calculation unit 133 may calculate the blood circulation volume data on the basis of RGB data prior to being converted to relative RGB data. Components having correlation with brain activity are more likely to be identified (statistical power is high) in blood circulation volume data calculated on the basis of RGB data prior to being converted to relative RGB data. As such, the blood circulation volume data calculated on the basis of RGB data prior to being converted to relative RGB data may be analyzed prior to the relative conversion blood circulation volume data calculated on the basis of relative RGB data. Additionally, a configuration is possible in which the blood circulation volume data is analyzed and components having significant correlation are extracted first and, then, only the components of the relative conversion blood circulation volume data that correspond to the extracted components are analyzed. In this case, computation load can be reduced.

(4-2-3) Modification Example 2C

In the description given above, the camera 121 was assumed to be a typical visible light range camera, but an infrared camera may also be used. In such cases, the infrared camera captures images by emitting infrared light and capturing the reflected waves thereof. The photographic image data of changes in the facial surface of the subject may be obtained in this manner. The present inventors found that there is correlation between the blood circulation volume data calculated from the photographic image data obtained from the reflection of the infrared light and the blood circulation volume data calculated using mainly the R component of each pixel included in the RGB data captured in the visible light region. Accordingly, it is also possible to estimate human brain activity using photographic image data obtained from the reflection of such infrared light.

(4-2-4) Modification Example 2D

A configuration was described above in which the evaluation device 110 includes the image data acquisition means 120 and the brain activity estimation means 130. However, the evaluation device according to the present embodiment is not limited to such a configuration. That is, the evaluation device according to the present embodiment may have any configuration, as long as it includes the blood circulation volume calculation unit 133, the analysis unit 134, and the estimation unit 135. Specifically, the evaluation device according to the present embodiment may take a form, including not only a form in which the device itself generates the image data by photographing, but also a form in which photographic image data is received from an external device to analyze it therein.

(4-3) Evaluation Means 200

The evaluation means 200 evaluate the degree of interest of the subject on the basis of the brain activity of the subject estimated by the brain activity estimation means 30 and/or the brain activity estimation means 130. For example, a configuration is possible in which the evaluation means 200 include an analysis unit 201 that evaluates the degree of interest of the subject in a stimulus (e.g. visual stimulation, auditory stimulation, tactile stimulation, olfactory stimulation, or taste stimulation) applied to the subject by analyzing changes in the amount of brain activity in response to that stimulus. The degree of interest is quantified on the basis of the degree of rise in the amount of brain activity estimated by the brain activity estimation means 30, 130 and the duration thereof from before to after applying the stimulus to the subject. For example, the degree of interest is evaluated to be low when there is absolutely no change in the amount of brain activity from before to after applying the stimulus to the subject, when the amount of brain activity rises but the degree of rise is small, or when the duration of the raised amount of brain activity is short. Meanwhile, the degree of interest is evaluated to be high when the amount of brain activity rises from before to after applying the stimulus to the subject and the degree of rise is large or the duration of the raised amount of brain activity is long. Note that, levels of the degree of interest may be appropriately configured in accordance with the use of the evaluation devices 10, 110, on the basis of the degree of rise and/or raised duration of the amount of brain activity.

As a result of the configuration, with the evaluation devices 10, 110, the brain activity of the subject is estimated on the basis of the facial skin temperature and/or the photographic images of the facial surface, and the degree of interest of the subject is evaluated on the basis of the estimated brain activity. Moreover, in cases where the evaluation means 200 include a notification unit 202 that notifies the administrator of the evaluation devices 10, 110 of information about the degree of interest of the subject, the administrator can ascertain, from the notification unit 202, the degree of interest of the subject in a predetermined stimulus. The notification unit 202 is not particularly limited, provided that it is capable of outputting the analyzed degree of interest to the administrator. Examples thereof include display devices that display images, messages, and the like, and audio output devices that output voice and buzzer sounds.

Additionally, in cases where acquiring various types of time-series data using the facial skin temperature acquisition means 20 and/or the image data acquisition means 120 after the analysis units 32, 134 have identified the components that reflect brain activity, the additionally acquired various types of data are decomposed into a plurality of components by singular value decomposition in the evaluation devices 10, 110, and only the identified components are analyzed. As a result, the degree of interest of the subject in a given stimulus can be evaluated in real time.

Furthermore, a configuration is possible in which the evaluation devices 10, 110 according to the present invention collectively acquire the facial skin temperature data and/or the photographic image data of the facial surfaces of a plurality of subjects, instead of only a specific individual subject. As a result, the interest levels of the plurality of subjects in a predetermined stimulus can be evaluated at once.

In addition, there are conventional techniques for acquiring heart rate information, biological information, and so on of the subject from the skin temperature or captured images of the facial surface of the subject. These conventional techniques can be applied to the components obtained by performing the singular value decomposition or the like on the various data obtained from the facial skin temperature acquisition means 20 and/or the image data acquisition means 120. As such, heart rate information, biological information, or the like can be accurately acquired. Accordingly, a configuration is possible in which the analysis unit 32 and/or the analysis unit 134 is provided with a feature for analyzing the plurality of components obtained from the singular value decomposition and acquiring heart rate information, biological information, or the like, and the estimation units 33, 135 of the embodiment described above are provided with features for estimating functions of the sympathetic nervous system/parasympathetic nervous system.

(5) Features 5-1

In the present embodiment, human brain activity is estimated on the basis of the time-series facial skin temperature data and/or facial blood circulation volume data acquired by the facial skin temperature acquisition means 20 and/or the image data acquisition means 120. As such, human brain activity can be estimated without using electroencephalogram electrodes or other sensors that require pretreatment before being applied. Accordingly, human brain activity can be easily estimated and the degree of interest of the subject can be evaluated on the basis of the estimated brain activity.

5-2

In cases where a situation is created in which the human brain is placed in states of activation and rest by actually giving and withholding the brain function activation task to a human while the time-series facial skin temperature data and/or the image data is being acquired, it can be said that there is a high possibility that the component having correlation between the component waveform of each component and the brain activated time and the brain resting time is a component indicating a change in skin temperature and/or blood circulation volume that reflects brain activity.

In the present embodiment, the brain function activation task is given to the individual for a certain period of time while the facial skin temperature acquisition means 20 and/or the image data acquisition means 120 is acquiring the time-series facial skin temperature data and/or the image data. That is, in the present embodiment, the brain function activation task is actually given to and withheld from the individual and, as a result, a situation is created in which the human brain is placed in an activated state and a resting state. Moreover, the various time-series data thusly acquired is decomposed into a plurality of components by the singular value decomposition, each component is evaluated whether there is correlation between the component waveform thereof and the brain activated time and the brain resting time, and a component evaluated as having correlation is extracted from the plurality of components as the determination component. Thus, compared, for example, to a case in which a predetermined component identified in prior experiments or the like is extracted from the plurality of components as the extraction component, the probability of extraction of a component, which is less related to the human brain activity, as an extraction component from the plurality of components, can be reduced.

5-3

The brain has a mechanism called the selective brain cooling system whereby the brain is cooled independently of body temperature. The selective brain cooling system is known to discharge heat generated by brain activity using the forehead and the area around the paranasal sinuses. When heat is discharged, a change in the facial skin temperature resulting from brain activity or the facial blood circulation volume that correlates to the facial skin temperature appears at the forehead and/or the area around the paranasal sinuses.

In the present embodiment, various data of the forehead and/or the area around the paranasal sinuses is analyzed and the determination component is extracted. As such, it is possible to accurately extract components related to human brain activity.

5-4

In the evaluation devices 10, 110 of the present embodiment, when the evaluation means 200 include the notification unit 202, the administrator is notified of information about the degree of interest of the subject. As a result, the administrator can ascertain the interest level of the subject.

(6) Use Examples of Evaluation Device

Next, use examples of the evaluation device according to the present invention will be described.

(6-1) Market Research Device

Next, an example is described of a case in which the evaluation devices 10, 110 according to the embodiment or the modification examples described above are used for market research. Market research devices are installed in event halls, stores, or product exhibition halls, and quantify the reactions of subjects, namely consumers, visitors, and the like, to products, events, and the like. In one example, the market research device includes the evaluation devices 10, 110, and market research storage means. The market research storage means store the results evaluated by the evaluation means 200 of the evaluation devices 10, 110 for each preset research period. For example, in a case in which the market research device is used to perform market research on a predetermined product or on a feature of the predetermined product, the degree of interest of that consumer in the predetermined product or the like can be quantified by presenting the predetermined product or feature thereof directly to the consumer so as to apply a visual stimulation of the predetermined product to the consumer, and then analyzing the change (degree of rise during this period of time) in the amount of brain activity during the period of time in which the visual stimulation was being applied. By setting, as the research period, the period of time in which the predetermined product or the like is being presented directly to the consumer, evaluation results of the degree of interest of the subject in the predetermined product or the like will be stored in the market research storage means. The administrator of the market research device can perform market research for the predetermined product or the like by analyzing the evaluation results notified by the notification unit 202. Thus, with the market research device, the degree of interest in, that is, the reaction to the predetermined product or the like can be evaluated by using non-contact means such as the facial skin temperature acquisition means and/or the image data acquisition means and applying an external stimulus such as visual stimulation to the subject.

Note that when applying the visual stimulation of the predetermined product to the consumer as described above, a digital signage device (display device) may be used. In this case, visual information about the product is displayed on a display panel of the digital signage device, and images of the face of the consumer, is in front of the display panel and looking at the visual information, are captured from the back side of the display panel or from directions above, below, to the left, and to the right. Then, the market research device evaluates the degree of interest of the subject observing the visual stimulation on the basis of the captured face images. As a result, the interest level of the subject in the predetermined product or the like can be easily evaluated at various types of commercial facilities.

Furthermore, a configuration is possible in which, instead of capturing face images of one consumer, face images of a plurality of consumers are captured. In this case, the facial skin temperature data acquisition means 20 and/or the image data acquisition means 120 described above collectively acquire the facial skin temperature data and/or the image data of the facial surfaces of a plurality of subjects. Moreover, by combining this data with facial recognition technology or the like, facial change information of each individual consumer is acquired. Highly accurate analysis results can be obtained, particularly in movie theaters and the like because, in such facilities, the positions of members of the audience are fixed and there is little facial movement.

(6-2) Learning Evaluation Device

Next, an example is described of a case in which the evaluation devices 10, 110 according to the embodiment or the modification examples described above are used for evaluations of learning. Learning evaluation devices can be used in schools, cram schools, companies, e-learning, hospitals, and the like to quantify the degree of interest, degree of concentration, or the like of a subject, that is, a student, on learning matter. In one example, the learning evaluation device includes the evaluation devices 10, 110 and learning evaluation storage means. The learning evaluation storage means store the results evaluated by the evaluation means 200 of the evaluation devices 10, 110 for each preset certain period of time.

For example, in a case where the learning evaluation device evaluates the concentration level of a subject on learning matter, a stimulus is applied by giving a task to the student and making the student work on the task, and changes (the degree of rise in this time period) in the amount of brain activity during the certain period of time are analyzed. As a result, the concentration level of the student on the learning matter being worked on can be quantified. Here, by setting the learning period as the certain period of time, the evaluation results of the concentration level of the student during the learning period will be stored in the learning evaluation storage means. The administrator of the learning evaluation device can evaluate the concentration level of the student on the learning matter by analyzing the evaluation results notified by the notification unit 202. Thus, with the learning evaluation device, the concentration level on or degree of interest in, that is, the reaction to the learning matter can be evaluated by using non-contact means such as the facial skin temperature acquisition means and/or the image data acquisition means and applying an external stimulus such as a task to the subject.

INDUSTRIAL APPLICABILITY

The present invention can easily estimate brain activity and, as such, is useful for applications to evaluation devices that evaluate the degree of interest of subjects on the basis of brain activity.

What is claimed is:

1. An estimation device, comprising:
    at least one of
        a facial skin temperature acquisition unit acquiring, in time-series, facial skin temperature data of a facial surface of a subject to which brain function activation information is provided, and
        a facial photographic image acquisition unit obtaining, in time-series, facial photographic image data obtained by imaging the facial surface of the subject to which the brain function activation information is provided; and
    an evaluation unit evaluating a degree of interest of the subject based on a change in an amount of brain activity based on at least one of the facial skin temperature data acquired by the facial skin temperature acquisition unit and the facial surface photographic image data acquired by the facial surface photographic image data acquisition unit.

2. The estimation device according to claim 1, further comprising:
    a decomposing unit decomposing at least one of the facial skin temperature data and the facial surface photographic image data into a plurality of components corresponding to at least a plurality of time distributions,
    the evaluation unit evaluating the degree of interest of the subject based on a determination component extracted from the plurality of components.

3. The evaluation device according to claim 2, wherein the decomposing unit decomposes at least one of the facial skin temperature data and the facial surface photographic image data into a plurality of components corresponding to a plurality of sets of time distributions and space distributions.

4. The estimation device according to claim 2, wherein the decomposing unit decomposes at least one of the facial skin temperature data and the facial surface photographic image data into a plurality of components by singular value decomposition, principal component analysis, or independent component analysis.

5. The estimation device according to claim 2, wherein the decomposing unit further
    extracts, from the plurality of components, a component having a waveform with an amplitude that has correlation with a brain activated time and a brain resting time as a determination component, and
    estimates the brain activity of the subject based on the determination component.

6. The evaluation device according to claim 1, wherein at least one of the facial skin temperature acquisition unit and the facial photographic image data acquisition unit acquires at least one of the facial skin temperature data and the facial photographic image data from at least one of a forehead and an area around the paranasal sinuses of the subject.

7. The estimation device according to claim 1, wherein at least one of the facial skin temperature acquisition unit and the facial photographic image data acquisition unit acquires at least one of the facial skin temperature data and the facial photographic image data of a plurality of subjects.

8. The estimation device according to claim 1, wherein the evaluation unit includes
    an analysis unit that analyzes a concentration level of the subject based on the brain activity of the subject, and
    a notification unit that notifies an administrator of the evaluation unit of information about the concentration level of the subject.

9. A market research device including the evaluation device according to claim 1, the market research device further comprising:
    a market research storage unit storing results evaluated by the evaluation unit for each preset research period.

10. The market research device according to claim 9, further comprising:
    a display device that displays visual information about a product.

11. A learning evaluation device including the evaluation device according to claim 1, the learning evaluation device further comprising:
    a learning evaluation storage unit storing results evaluated by the evaluation unit for each preset learning period.

* * * * *